United States Patent
Hazen et al.

(10) Patent No.: US 11,331,280 B2
(45) Date of Patent: *May 17, 2022

(54) METHODS FOR INHIBITING CONVERSION OF CHOLINE TO TRIMETHYLAMINE (TMA)

(71) Applicants: The Procter & Gamble Company, Cincinnati, OH (US); The Cleveland Clinic Foundation, Cleveland, OH (US)

(72) Inventors: Stanley Leon Hazen, Cleveland, OH (US); Jose Carlos Garcia-Garcia, Cincinnati, OH (US); Jodie Michelle Reed, Loveland, OH (US); Lori Ann Reinsalu, Cincinnati, OH (US); Vincent Peter Sica, Loveland, OH (US); Timothy R Baker, Liberty Township, OH (US)

(73) Assignees: The Procter & Gamble Company, Cincinnati, OH (US); The Cleveland Clinic Foundation, Cleveland, OH (US)

( * ) Notice: Subject to any disclaimer, the term of this patent is extended or adjusted under 35 U.S.C. 154(b) by 235 days.

This patent is subject to a terminal disclaimer.

(21) Appl. No.: 16/675,267

(22) Filed: Nov. 6, 2019

(65) Prior Publication Data
US 2020/0138740 A1    May 7, 2020

Related U.S. Application Data

(60) Provisional application No. 62/850,670, filed on May 21, 2019, provisional application No. 62/828,688, filed on Apr. 3, 2019, provisional application No. 62/756,259, filed on Nov. 6, 2018.

(51) Int. Cl.
| | |
|---|---|
| *A61K 31/10* | (2006.01) |
| *A61K 36/28* | (2006.01) |
| *A61P 9/10* | (2006.01) |
| *A61P 7/12* | (2006.01) |
| *A61P 25/28* | (2006.01) |

(52) U.S. Cl.
CPC .............. *A61K 31/10* (2013.01); *A61K 36/28* (2013.01)

(58) Field of Classification Search
CPC ......... A61K 31/10; A61K 36/28; A61P 25/28; A61P 7/12; A61P 9/10
See application file for complete search history.

(56) References Cited

U.S. PATENT DOCUMENTS

| | | |
|---|---|---|
| 2010/0028551 A1 | 2/2010 | Lee |
| 2017/0151208 A1 | 6/2017 | Hazen et al. |
| 2017/0151250 A1 | 6/2017 | Hazen et al. |
| 2017/0152222 A1 | 6/2017 | Garcia-garcia |
| 2018/0000754 A1 | 1/2018 | Hazen |
| 2018/0099384 A1 | 4/2018 | Dahl |
| 2019/0099389 A1 | 4/2019 | Garcia-garcia |
| 2019/0099390 A1 | 4/2019 | Garcia-garcia |
| 2020/0138887 A1 | 5/2020 | Hazen et al. |

FOREIGN PATENT DOCUMENTS

| | | |
|---|---|---|
| WO | WO2013188417 A2 | 12/2013 |
| WO | WO2017095993 A1 | 6/2017 |
| WO | 2018004945 A1 | 1/2018 |

OTHER PUBLICATIONS

Carlé JS, Christophersen C. Dogger bank itch. 4. An eczema-causing sulfoxonium ion from the marine animal, Alcyonidium gelatinosum [Bryozoa], Toxicon. 1982;20(1):307-10. doi: 10.1016/0041-0101(82)90232-x. PMID: 6210974. (Year: 1982).*

International Search Report and Written Opinion, PCT/US2019/059982, dated Mar. 20, 2020, 14 pgs.

International Search Report and Written Opinion, PCT/US2019/059984, dated Mar. 20, 2020, 12 pgs.

Wang et al., "Non-lethal inhibition of gut microbial trimethylamine production for the treatment of atherosclerosis", Cell, Author Manuscript, Dec. 17, 2015, 163 (7): pp. 1-21.

Yamazaki et al., "Effects of the dietary supplements, activated charcoal and copper chlorophyllin, on urinary excretion of trimethylamine in Japanese trimethylaminuria patients", Life Sciences, 74, 2004, pp. 2739-2747.

Luciane C. Rufatto et al. "Genus Mikania: chemical composition andphytotherapeutical activity" Revista Brasileira de Farmacognosiabrazilian Journal of Pharmacognosy,vol. 22, Nov. 1, 2012 (Nov. 1, 2012), pp. 1384-1403, XP55678116, DOI: 10.1590/50102, 20 Pages.

The Procter & Gamble Company, The Cleveland Clinic Foundation, U.S. Appl. No. 16/675,264, filed Nov. 6, 2019.

* cited by examiner

*Primary Examiner* — Jeffrey S Lundgren
*Assistant Examiner* — Chris E Simmons
(74) *Attorney, Agent, or Firm* — James E Oehlenschlager

(57) ABSTRACT

A method of inhibiting the conversion of choline to trimethylamine (TMA) and lowering TMAO in an individual by providing a composition comprising (2-hydroxyethyl) dimethylsulfonium with a counterion wherein the counterion is selected from chloride, bromide or iodide.

5 Claims, No Drawings
Specification includes a Sequence Listing.

METHODS FOR INHIBITING CONVERSION OF CHOLINE TO TRIMETHYLAMINE (TMA)

FIELD OF THE INVENTION

The invention generally relates to materials and methods for inhibiting trimethylamine production in an individual.

BACKGROUND

Trimethylamine (TMA) and its derivative trimethylamine N-oxide (TMAO) are metabolites linked to disorders such as kidney disease, insulin resistance, diabetes mellitus, obesity, Alzheimer's disease, dementia, cognitive impairment, non-alcoholic steatohepatitis (NASH), trimethylaminuria, and cardiovascular diseases (CVD). TMA is produced in the gut by bacteria which are capable of converting substrates including but not limited to choline, to TMA. There is an unmet need for compositions which inhibit the production of TMA by bacteria.

CVD is a general term encompassing a range of conditions affecting the heart and blood vessels, including atherosclerosis, coronary heart disease, cerebrovascular disease, heart failure, cardiomyopathy, atherothrombotic disease, aorto-iliac disease, and peripheral vascular disease. CVD is generally associated with conditions that involve narrowed, blocked, aneurysmal or dissection of one or more blood vessels, or thrombosis (blood clot formation). Complications associated with CVD include, but are not limited to, myocardial infarction, stroke, angina pectoris, acute coronary syndrome, transient ischemic attacks, congestive heart failure, aortic aneurysm, atrial fibrillation or flutter, ventricular arrhythmias, cardiac conduction abnormalities, need for revascularization and death. Revascularization can include but is not limited to angioplasty, stenting, coronary artery bypass grafting, repair or replacement of vascular shunt or access such as an arteriovenous fistula. Complications associated with atherothrombotic disease include, but are not limited to, myocardial infarction, stroke, pulmonary embolism, deep venous thrombosis. According to the World Health Organization, CVDs are the leading cause of death globally, with over 75% of deaths occurring in low- and middle-income countries. World Health Organization Fact Sheet No. 317, updated January 2015. The World Health Organization projects that diabetes will be the seventh leading cause of death in 2030. World Health Organization Fact Sheet No. 312, updated January 2015. Prevention and management of conditions associated with TMA and TMAO, including CVD and diabetes, is a major public health concern.

The use of plant extracts to treat various conditions and diseases is an accepted part of both traditional medicine and modern treatments. Members of the genus *Mikania*, part of the Asteraceae family, are found distributed through Southern and Central America. Example species include *M. guaco* Bonpl., *M. micrantha, M. cordifolia, M. trinervis, M. trachypleura, M. grazielae, M. sessilifolia, M. speciosa*, and *M. scandens*. There are reports of extracts from different *Mikania* species having effects in various disease-related pathways, including anti-inflammatory benefits, antibacterial effects, treatment of snakebites, and analgesic effects. Brigida da Silva A S, Owiti A O, Barbosa W L. Pharmacology of *Mikania* genus: A systematic review. Phcog Rev 2018; 12:230-237; Rufatto L C, Gower A, Schwambach J, Moura S. Genus *Mikania*: chemical composition and phytotherapeutical activity. Brazilian Journal of Pharmacognosy 2012; 22(6): 1384-1403. However, there are no known reports of extracts from species of *Mikania* that inhibit the conversion of choline to TMA.

SUMMARY OF THE INVENTION

The disclosure is based, at least in part, on the discovery that extracts of the plants from the *Mikania* genus inhibit choline metabolism by gut or digestive tract microbiota resulting in reduction in the formation of trimethylamine (TMA). We have surprisingly found that extracts of *Mikania guaco* Bonpl. inhibit conversion of choline to TMA, in vivo and in vitro. The disclosure provides compositions and methods for, e.g., inhibiting the conversion of choline to TMA in vitro and in vivo, for improving or maintaining cardiovascular, cerebrovascular, or peripherovascular health, and for improving or preventing a condition associated with TMA and TMAO. In certain aspects, the invention provides one or more methods of inhibiting the conversion of choline to TMA in an individual.

In certain aspects, the invention provides one or more methods of reducing the production of TMAO comprising inhibiting the conversion of choline to TMA by a bacterium, by providing an extract of *Mikania*. The invention provides a method of inhibiting the conversion of choline to TMA in an individual. The method comprises administering to the individual a composition comprising an extract of *Mikania*.

The invention further provides a method of improving or maintaining cardiovascular health and wellness. A method may comprise administering to the individual a composition comprising an extract of *Mikania* as described herein in an amount that improves or maintains cardiovascular health. The invention also provides a method of improving a condition associated with the conversion of choline to TMA in an individual. The method comprises administering to the individual a composition comprising an extract of *Mikania*, as described herein in an amount effective to improve the condition. In some embodiments, the condition may be trimethylaminuria, reduced or impaired kidney function, kidney disease, chronic kidney disease (CKD), end-stage renal disease (ESRD), insulin resistance, diabetes mellitus, obesity, Alzheimer's disease, dementia, cognitive impairment, non-alcoholic steatohepatitis (NASH), or cardiovascular disease such as angina, arrhythmia, atherosclerosis, cardiomyopathy, congestive heart failure, coronary artery disease (CAD), carotid artery disease, endocarditis, coronary thrombosis, myocardial infarction (MI), high blood pressure/hypertension, hypercholesterolemia/hyperlipidemia, peripheral artery disease (PAD), or stroke. In some embodiments, the condition is adverse ventricular remodeling, ventricular systolic dysfunction, ventricular diastolic dysfunction, cardiac dysfunction, ventricular arrhythmia, or cardiovascular disease or atherosclerosis due to oral biofilm formation and periodontal disease.

The invention further provides the extract of *Mikania* for use in inhibiting the conversion of choline to TMA in vivo or in vitro, for improving or maintaining cardiovascular health, and for improving a condition associated with the conversion of choline to TMA; and use of the compositions comprising an extract of *Mikania* for inhibiting the conversion of choline to TMA in vivo or in vitro, for improving or maintaining cardiovascular health, and for improving a condition associated with the conversion of choline to TMA.

The foregoing summary is not intended to define every aspect of the invention, and additional aspects are described in other sections, such as the Detailed Description. In addition, the invention includes, as an additional aspect, all embodiments of the invention narrower in scope in any way than the variations defined by specific paragraphs set forth herein. For example, certain aspects of the invention are described as a genus, and it should be understood that every member of a genus is, individually, an aspect of the invention. Also, aspects described as a genus or selecting a member of a genus should be understood to embrace combinations of two or more members of the genus. In certain aspects, the invention may be described as related to a substrate, for example choline, and may also relate to metabolites or precursors of said substrate, for example precursors or metabolites of choline such as lecithin, phosphatidylcholine, phosphorylcholine or glycerophosphocholine.

With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise, for example X or Y, means X or Y or both. If aspects of the invention are described as "comprising" a feature, embodiments also are contemplated "consisting of" or "consisting essentially of" the feature.

DETAILED DESCRIPTION OF THE INVENTION

The components of the present inventions are described in the following paragraphs.

The present invention provides one or more methods of reducing the production of TMA comprising: inhibiting the conversion of choline to TMA by a bacterium using a composition comprising an extract or multiple extracts of *Mikania*. Such compositions or extracts of *Mikania* may be used to inhibit the conversion of choline to TMA in vivo or in vitro, or inhibit the production of TMA by bacteria, or to shift the composition of polymicrobial mixtures of bacteria (such as in the intestines) towards communities less capable of generating TMA. The shift in composition of polymicrobial mixtures of bacteria may be due to reduced proliferation of species of bacteria that favor choline and/or choline related compounds as a metabolic substrate. The extract or extracts of *Mikania*, and composition or compositions comprising an extract or multiple extracts of *Mikania* may be administered to an individual in an amount effective to inhibit the production of TMA and TMAO by bacteria in the gut or digestive tract of an individual, for example from substrates including but not limited to choline.

TMA synthesized by bacteria resident in the gut of mammals is oxidized in the liver and other tissues that express flavin monooxygenases (FMOs) including but not limited to adipose tissue, to trimethylamine N-oxide (TMAO, TMANO). Exemplary precursors of TMA include choline, betaine, phosphatidylcholine, phosphocholine, glycerophosphocholine, carnitine, L-carnitine, TMAO, sphingomyelin, and lecithin, many of which are derived from dietary sources such as, for example, whole eggs and beef liver. These sources may act as substrates for bacteria that can metabolize them to TMA. Without wishing to be bound to a particular mechanism or biochemical pathway, the anaerobic conversion of choline to TMA is facilitated by a glycyl radical enzyme homologue, choline trimethylamine-lyase (CutC). Craciun et al., Proc. Natl. Acad. Sci. (2012), 109: 21307-21312. The reduction of choline conversion to TMA by bacteria in the gut of an individual leads to a reduction in TMA absorption from the gut, leading to a subsequent reduction in plasma TMAO following oxidation of TMA to TMAO by the flavin monooxygenase 3 (FMO3) enzyme in the liver. Wang et al., Nature (2011), 472: 57-63. Lower plasma TMAO levels are related to a lower incidence of major cardiovascular events in humans. Tang et al., New England Journal of Medicine (2013) 368: 1575-1584. The conversion of choline to TMA may be mediated by one species of bacteria or comprise a multi-step process involving two, three or more species of bacteria.

As described previously, the present invention is based, at least in part, on the discovery that extracts of *Mikania* interfere with choline metabolism by gut microbiota resulting in reduction in the formation of TMA and trimethylamine N-oxide (TMAO). The disclosure provides compositions and methods that for example inhibit the conversion of choline to TMA in vitro and in vivo, improve or maintain cardiovascular, cerebrovascular, and peripherovascular health, and improve or prevent a condition associated with increased TMA and TMAO. Other conditions associated with increased levels of TMA may include production of TMA by bacteria in the vagina leading to vaginal odor, or production of TMA by bacteria on the body leading to body odor, or production of TMA by bacteria in the mouth leading to bad breath or oral care biofilm development, or during pregnancy where the third trimester and post-partum period are associated with an increased risk of thrombosis, thus lowering TMA and TMAO levels may reduce this risk. The disclosure additionally provides compositions and methods to increase the availability of choline in the gut of an individual with a condition where increased choline availability would be beneficial, by inhibiting choline catabolism. One such condition is during pregnancy and the post-partum period where increased choline availability in the gut of the mother may promote brain development for the fetus and newborn.

Conversion of choline to TMA by gut bacteria has been attributed to the glycyl radical enzyme homologue, choline trimethylamine-lyase CutC. Craciun et al. (2014) ACS Chem Biol 9: 1408-1413. It has been described that not all gut microbes contain the gene cluster including CutC. Martinez-del Campo et al. (2015) mBio 6(2):e00042-15. doi: 10.1128/mBio.00042-15. The cut gene cluster contains a set of genes encoding the glycyl radicle enzyme CutC, and a glycyl radicle activating protein CutD, cutC/D gene cluster. Craciun et al. (2012) PNAS 109:21307-21312.

In contrast, most sequenced bacteria convert choline to glycine betaine (GB, or trimethylglycine) which primarily acts as an osmoprotectant. Additionally, some bacteria can convert choline to GB and then to glycine, which may be used as a source of carbon and nitrogen. Wargo (2013) Appl. Environ. Microbiol. 79:2112-2120. *Pseudomonas aeruginosa* is one such species of bacteria that can convert choline to glycine via GB, dimethyl glycine (DMG) and sarcosine.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified. Room Temperature (RT) is considered to be 25° C.

The components of the present compositions are described in the following paragraphs.

As used herein, "dose" refers to a volume of medication, formulation, or dietary supplement, such as liquid formulation or oral dosage unit, containing an amount of a compound, ingredient or extract, for example a biological extract suitable for administration on a single occasion, according to sound medical practice or consumer guidelines. A dose can be orally administered. In one example, a dose can be a liquid medication and can be about 30 mL, in another example about 25 mL, in another example about 20 mL, in another example about 15 mL, and in another example about 10 mL, and in another example about 5 mL. In another example, a dose of liquid medication can be from about 5 mL to about 75 mL, in another example from about 10 mL to about 60 mL, in another example from about 15 mL to about 50 mL, in another example from about 25 mL to about 40 mL, and in another example from about 28 mL to about 35 mL. In another example, the dose can be a solid dosage form and can be from about 25 mg to about 5 g, in another example from about 1 g to about 10 g. in another example from about 2 g to about 15 g, in another example from about 100 mg to about 3 g, in another example from about 250 mg to about 2 g, in another example from about 500 mg to about 1.6 g, and in another example from about 750 mg to about 1 g. In addition, a dose may be a solid dosage form wherein the doses are different amounts, for example, one dose is about 3 g or a dose can be about 1.6 g. The concentration of ingredients can be adjusted to provide the proper doses of ingredients given the liquid or solid dose size. In certain embodiments, a dose can be administered about every 4 hours, about every 6 hours, about every 8 hours, about every 12 hours, or about every 24 hours.

In various embodiments, a dose administered in an amount effective to achieve the desired effect, e.g., inhibit conversion of choline to TMA, improve or maintain cardiovascular health, or improve a condition associated with conversion of choline to TMA, comprises between about 1 µg extract of *Mikania* to about 500 mg extract of *Mikania*, or between about 1 µg extract of *Mikania* to about 50 mg extract of *Mikania*, or between about 1 µg extract of *Mikania* to about 5 mg extract of *Mikania*, or between about 1 µg extract of *Mikania* to about 0.5 mg extract of *Mikania*, or between about 10 µg extract of *Mikania* to about 500 mg extract of *Mikania*, or between about 100 µg extract of *Mikania* to about 500 mg extract of *Mikania*, or between about 1 mg extract of *Mikania* to about 500 mg extract of *Mikania*, or between about 10 mg extract of *Mikania* to about 500 mg extract of *Mikania*, or between about 100 mg extract of *Mikania* to about 500 mg extract of *Mikania*, or between about 250 mg extract of *Mikania* to about 500 mg extract of *Mikania*, or between about 10 µg extract of *Mikania* to about 250 mg extract of *Mikania*, or between about 100 µg extract of *Mikania* to about 250 mg extract of *Mikania*, or between about 100 µg extract of *Mikania* to about 100 mg extract of *Mikania*, or between about 1 mg extract of *Mikania* to about 100 mg extract of *Mikania*, or between about 1 mg extract of *Mikania* to about 10 mg extract of *Mikania*, or between about 10 mg extract of *Mikania* to about 100 mg extract of *Mikania*.

In various embodiments, a dose comprises between about 0.1 µg to about 50 mg of (2-hydroxyethyl) dimethylsulfonium, or between about 0.1 µg to about 5 mg of (2-hydroxyethyl) dimethylsulfonium, or between about 0.1 µg to about 2.5 mg of (2-hydroxyethyl) dimethylsulfonium, or between about 0.1 µg to about 1 mg of (2-hydroxyethyl) dimethylsulfonium, or between about 0.1 µg to about 0.5 mg of (2-hydroxyethyl) dimethylsulfonium, or between about 0.1 µg to about 0.05 mg of (2-hydroxyethyl) dimethylsulfonium, or between about 0.1 µg to about 0.1 mg of (2-hydroxyethyl) dimethylsulfonium, or between about 0.1 µg to about 0.01 mg of (2-hydroxyethyl) dimethylsulfonium, or between about 1 µg to about 50 mg of (2-hydroxyethyl) dimethylsulfonium, or between about 1 µg to about 5 mg of (2-hydroxyethyl) dimethylsulfonium, or between about 1 µg to about 2.5 mg of (2-hydroxyethyl) dimethylsulfonium, or between about 1 µg to about 1 mg of (2-hydroxyethyl) dimethylsulfonium, or between about 1 µg to about 0.5 mg of (2-hydroxyethyl) dimethylsulfonium, or between about 1 µg to about 0.05 mg of (2-hydroxyethyl) dimethylsulfonium, or between about 1 µg to about 0.1 mg of (2-hydroxyethyl) dimethylsulfonium, or between about 1 µg to about 0.01 mg of (2-hydroxyethyl) dimethylsulfonium, about 5 µg to about 50 mg of (2-hydroxyethyl) dimethylsulfonium, or between about 5 µg to about 5 mg of (2-hydroxyethyl) dimethylsulfonium, or between about 5 µg to about 2.5 mg of (2-hydroxyethyl) dimethylsulfonium, or between about 5 µg to about 1 mg of (2-hydroxyethyl) dimethylsulfonium, or between about 5 µg to about 0.5 mg of (2-hydroxyethyl) dimethylsulfonium, or between about 5 µg to about 0.05 mg of (2-hydroxyethyl) dimethylsulfonium, or about 0.1 µg of (2-hydroxyethyl) dimethylsulfonium, or about 1 µg of (2-hydroxyethyl) dimethylsulfonium, or about 2 µg of (2-hydroxyethyl) dimethylsulfonium, or about 5 µg of (2-hydroxyethyl) dimethylsulfonium, or about 10 µg of (2-hydroxyethyl) dimethylsulfonium, or about 50 µg of (2-hydroxyethyl) dimethylsulfonium, or about 100 µg of (2-hydroxyethyl) dimethylsulfonium, or about 0.5 mg of (2-hydroxyethyl) dimethylsulfonium, or about 1 mg of (2-hydroxyethyl) dimethylsulfonium, or about 2.5 mg of (2-hydroxyethyl) dimethylsulfonium, or about 5 mg of (2-hydroxyethyl) dimethylsulfonium, or about 10 mg of (2-hydroxyethyl) dimethylsulfonium, or about 25 mg of (2-hydroxyethyl) dimethylsulfonium, or about 50 mg of (2-hydroxyethyl) dimethylsulfonium.

As used herein, "medication" refers to compositions comprising an extract of *Mikania*, such as pharmaceuticals, including prescription medications, over-the-counter medications, behind-the-counter medications and combinations thereof. In some examples, a medication can be a dietary supplement which can contain botanical materials, botanical extracts, vitamins, minerals, and supplements (VMS) including dietary supplements or ingredients such as botanicals.

Medication compositions can be in any suitable form including liquid compositions and solid oral dosage forms. Non-limiting examples of liquid compositions can include syrups, beverages, supplemental water, foam compositions, gel compositions, particles suspended in a liquid formulation, a solid in a gelatin or foam, saline wash and combinations thereof. Non-limiting examples of solid oral dosage forms can include tablets, capsules, caplets, sachets, sublingual dosage forms, buccal dosage forms, soft gels, and other liquid filled capsules, dissolvable dosage forms including dissolvable strips, films, gums including a center filled gum, gummies including a center filled gummy, lozenges, center filled tablets, powder, granules, pellets, microspheres, nanospheres, beads, or nonpareils, and combinations thereof. Tablets can include compressed tablets, chewable tablets, dissolvable tablets, and the like. In some examples, the medication can be applied to the skin, in an ointment such as a petroleum jelly-based ointment. In some examples the medication may be provided in a delivery device. In other examples, the medication can be inhaled, such as a nose spray or inhaler. In still other examples, the medication can be in a drink, such as a warm beverage. In further examples, the medication can contain a pharmaceutical active.

The medications can be in a form that is directly deliverable to the mouth, throat, or skin. In some embodiments, the medication compositions can be delivered by a delivery device selected from droppers, pump, sprayers, liquid dropper, saline wash delivered via nasal passageway, cup, bottle, canister, pressurized sprayers, atomizers, air inhalation devices, squeezable sachets, power shots, blister cards, and other packaging and equipment, and combinations thereof. The sprayer, atomizer, and air inhalation devices can be associated with a battery or electric power source.

As used herein the term "individual" includes both humans and other types of mammals sharing the TMAO pathway, such as domesticated animals, including but not limited to, domestic dogs (canines), cats (feline), horses, cows, ferrets, rabbits, pigs, rats, mice, gerbils, hamsters, horses, and the like.

A wide variety of individuals may wish to reduce the level of TMA produced by bacteria in their gut or digestive tract. For example, individuals diagnosed with cardiovascular disease may be directed by a physician to take prescription drugs or effect lifestyle changes to modulate blood cholesterol or TMAO levels to reduce the risk of serious cardiovascular events. Other individuals not previously diagnosed with cardiovascular disease but who wish to improve or maintain cardiovascular health may also wish to reduce the level of TMA produced by digestive tract bacteria. As described further herein, a reduction in TMA (and, by extension, TMAO) is achieved by the compositions described herein, which may include, for example, a dietary supplement comprising the extract of *Mikania*.

The disclosure includes, a method of inhibiting the conversion of choline to TMA, a method of improving cardiovascular health, and a method of improving a condition associated with conversion of choline to TMA comprising administering to the individual a composition comprising an extract of *Mikania*. Features of the compositions and methods are described below. Section headings are for convenience of reading and not intended to be limiting per se. The entire document is intended to be related as a unified disclosure, and it should be understood that all combinations of features described herein are contemplated, even if the combination of features are not found together in the same sentence, or paragraph, or section of this document. It will be understood that any feature of the methods, extracts or compositions described herein can be deleted, combined with, or substituted for, in whole or part, any other feature described herein.

Mikania

In certain embodiments, the *Mikania* according to this invention comprises plants of the *Mikania* genus with greater than 94% sequence identity to SEQ ID NO. 1, and/or greater than 94% sequence identity to SEQ ID NO. 2. In one aspect of the invention the *Mikania* comprises plants from the species *M. guaco* Bonpl., *M. micrantha*, *M. trinervis*, *M. cordifolia*, *M. grazielae*, *M. sessilifolia*, *M. speciosa*, or *M. trachypleura*, and combinations thereof. Additionally, the *Mikania* according to the invention includes plants from the species *M. guaco* Bonpl., *M. micrantha*, *M. trinervis*, *M. cordifolia*, *M. grazielae*, *M. sessilifolia*, *M. speciosa*, *M. trachypleura*, *M. thapsoides*, *M. hemisphaerica*, *M. ternata*, *M. hastato-cordata*, or *M. campanulate*, and combinations thereof. Herein, 'sequence identity' is determined by aligning two subject polypeptide (amino acid) or polynucleotide (nucleic acid, DNA or RNA) sequences for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 50%, more preferably at least 60%, and even more preferably at least 70%, 80%, or 90%, and even more preferably at least 90%, 91%, 92%, 93%, 94%, or 95% of the length of the reference sequence (i.e., where 100% equals the entire coding sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, disregarding the number of gaps, and the length of each gap, which need to be introduced for optimal alignment of the two sequences.

| SEQ ID NO | Sequence |
|---|---|
| 1 | *Mikania guaco* ETS (external transcribed spacer) region |
| 2 | *Mikania guaco* ITS (internal transcribed spacer) region |

A sequence listing that sets forth the nucleotide sequences for SEQ ID NO: 1 and 2 is being filed concurrently with the present application as a text file titled "15401M2_&_Seq_ST25." The text file was created on 5 Nov. 2019 and is 1.81 Kbytes in size.

Extracts

The methods of the present invention comprise administering to the individual an extract of *Mikania* or a composition comprising an extract of *Mikania*. The extract may be generated or derived from the whole plants, different parts of the plant including but not limited to leaf, root, stem, aerial parts (i.e. those that grow above ground), subterranean parts (i.e. those that grow below ground), seeds, germinated seeds, plumule, whole flowers or parts of flowers (i.e. petals, stamen), bark, or combinations thereof. The parts of whole plant or parts of the plant may be fresh, frozen, frozen at 0° C. or −20° C. or −70° C., or between 0° C. and −70° C., stored in liquid nitrogen, dried, milled, powdered, refrigerated, dehydrated, or a combination thereof.

In some embodiments, the extract is prepared by using solvents including but not limited to water, dimethylsulfoxide (DMSO), methanol, ethanol, ethyl acetate, hexane, or a combination thereof. In embodiments, the extract is prepared using an alcohol-based solvent. In embodiments, the extract is prepared using an alcohol-aqueous solvent. In embodiments, the extract is prepared by supercritical fluid extraction. An example of supercritical fluid extraction is the use of supercritical carbon dioxide.

The extract of *Mikania* or a composition comprising an extract of *Mikania* is administered in an amount effective to achieve the desired effect, e.g., inhibit conversion of choline to TMA, improve or maintain cardiovascular health, or improve a condition associated with conversion of choline to TMA.

In various embodiments, the extract of *Mikania* or composition comprising an extract of *Mikania* demonstrates an $IC_{50}$ of $1\times10^{-3}$ or less, $5\times10^{-3}$ or less, $1\times10^{4}$ or less, $5\times10^{4}$ or less, $1\times10^{-5}$ or less, $5\times10^{-5}$ or less, or $1\times10^{-6}$ or less, or $1\times10^{-7}$ or less, or $1\times10^{-8}$ or less, or $1\times10^{-9}$ or less, or $1\times10^{-10}$ or less or $1\times10^{-11}$ or less or $1\times10^{-12}$ or less, or between $1\times10^{-9}$ and $1\times10^{-3}$, or between $1\times10^{-12}$ and $1 \times 10^{-9}$, or between $1 \times 10^{-9}$ and $1 \times 10^{-6}$, or between $1 \times 10^{-8}$ and $1 \times 10^{-6}$, or between $1 \times 10^{-6}$ and $1 \times 10^{-3}$, between $1 \times 10^{-6}$ and $1 \times 10^{4}$, between $1 \times 10^{-6}$ and $1 \times 10^{-5}$, between $1 \times 10^{-5}$ and $1 \times 10^{-3}$, or between $1 \times 10^{-4}$ and $1 \times 10^{-3}$, or between $1.7 \times 10^{-11}$ and $1 \times 10^{-7}$, (observed 50% inhibition of TMA (or TMAO) formation from choline; mg/mL. Data may also be represented as g/mL), in the assay described in EXAMPLE 2, EXAMPLE 3, or EXAMPLE 5. In various embodiments, the composition comprising an extract of *Mikania* demonstrates an $IC_{50}$ of between $1 \times 10^{-11}$ and $1 \times 10^{-7}$, or between $1 \times 10^{-8}$ to $1 \times 10^{-3}$, or between $1.2 \times 10^{-6}$ to $2 \times 10^{-3}$, or between $1 \times 10^{-6}$ to $1 \times 10^{4}$ (observed 50% inhibition of TMA formation from choline; mg/mL. Data may also be represented as g/mL) as measured in the assay described in EXAMPLE 2, EXAMPLE 3 or EXAMPLE 5.

In various embodiments, the extract of *Mikania* or composition comprising an extract of *Mikania* demonstrates an $EC_{50}$ of $1 \times 10^{-3}$ or less, $5 \times 10^{-3}$ or less, $1 \times 10^{4}$ or less, $5 \times 10^{4}$ or less, $1 \times 10^{-5}$ or less, $5 \times 10^{-5}$ or less, or $1 \times 10^{-6}$ or less, or $1 \times 10^{-7}$ or less, or $1 \times 10^{-8}$ or less, or $1 \times 10^{-9}$ or less, or $1 \times 10^{-10}$ or less or $1 \times 10^{-11}$ or less or $1 \times 10^{-12}$ or less, or between $1 \times 10^{-9}$ and $1 \times 10^{-3}$, or between $1 \times 10^{-12}$ and $1 \times 10^{-9}$, or between $1 \times 10^{-9}$ and $1 \times 10^{-6}$, or between $1 \times 10^{-8}$ and $1 \times 10^{-6}$, or between $1 \times 10^{-6}$ and $1 \times 10^{-3}$, between $1 \times 10^{-6}$ and $1 \times 10^{4}$, between $1 \times 10^{-6}$ and $1 \times 10^{-5}$, between $1 \times 10^{-5}$ and $1 \times 10^{-3}$, or between $1 \times 10^{-4}$ and $1 \times 10^{-3}$, or between $1.7 \times 10^{-11}$ and $1 \times 10^{-7}$, (observed 50% inhibition of TMA (or TMAO) formation from choline; mg/kg), in the assays described in EXAMPLE 6. In various embodiments, the composition comprising an extract of *Mikania* demonstrates an $EC_{50}$ of between $1 \times 10^{-11}$ and $1 \times 10^{-7}$, or between $1 \times 10^{-8}$ to $1 \times 10^{-3}$, or between $1.2 \times 10^{-6}$ to $2 \times 10^{-3}$, or between $1 \times 10^{-6}$ to $1 \times 10^{4}$ (observed 50% inhibition of TMA formation from choline; mg/kg) as measured in the assays described in EXAMPLE 6.

In various embodiments, the extract of *Mikania* comprises greater than 10 ng/mL of (2-hydroxyethyl) dimethylsulfoxonium, or greater than 50 ng/mL, or greater than 100 ng/mL, or less than 500 mg/mL, or less than 100 mg/mL, or less than 10 mg/mL, or between 10 ng/mL and 500 mg/mL, or between 10 ng/mL and 100 mg/mL, or between 10 ng/mL and 1 mg/mL, or between 10 ng/mL and 500 µg/mL, or between 10 ng/mL and 125 µg/mL or between 10 ng/mL and 100 µg/mL, or between 10 ng/mL and 10 µg/mL, or between 10 ng/mL and 1 µg/mL, or between 10 ng/mL and 500 ng/mL, or between 10 ng/mL and 100 ng/mL, or between 50 ng/mL and 500 mg/mL, or between 50 ng/mL and 100 mg/mL, or between 50 ng/mL and 1 mg/mL, or between 50 ng/mL and 500 µg/mL, or between 50 ng/mL and 125 µg/mL or between 50 ng/mL and 100 µg/mL, or between 50 ng/mL and 10 µg/mL, or between 50 ng/mL and 1 µg/mL, or between 50 ng/mL and 500 ng/mL, or between 50 ng/mL and 100 ng/mL of (2-hydroxyethyl) dimethylsulfoxonium. In one embodiment, the starting extract comprises 25 mg biological raw material per 1 mL methanol, when tested according to EXAMPLE 8.

The invention includes a method of inhibiting the conversion of choline to TMA in an individual which comprises administering to an individual an extract of *Mikania* or a composition comprising an extract of *Mikania*, as described previously. In certain embodiments, as described herein, an individual may be in need of reduced TMA levels, improvement of cardiovascular health, and the like. An individual may exhibit an elevated level of TMA or a metabolite thereof (e.g., TMAO, dimethylamine (DMA), or monomethylamine (MMA)) prior to administration. In various embodiments, an individual suffers from cardiovascular disease, ingests a diet high in choline, or exhibits one or more CVD risk factors (e.g., smoking, stress, high total cholesterol, high LDL cholesterol, low HDL (high density lipoproteins) cholesterol, age, hypertension, family history of CVD, obesity, prediabetes, diabetes, or the like).

A method of inhibiting the conversion of choline to TMA in vitro is also contemplated. For example, a method may comprise contacting a bacterium, such as a bacterium that is represented in the gut microflora, or a bacterial lysate that metabolizes choline to produce TMA with a composition comprising an extract of *Mikania*, as described previously. In various embodiments, a bacterium may be selected from *Proteus mirabilis*, *Desulfovibrio alaskensis*, *Clostridium ljungdahlii*, *C. scindens*, *C. aldenense*, *C. aminobutyricum*, *Collinsella tanakaei*, *Anaerococcus vaginalis*, *Streptococcus dysgalactiae*, *Desultitobacterium hafniense*, *Klebsiella variicola*, *K. pneumonia*, *P. penneri*, *Eggerthella lento*, *Edwardsiella tarda*, *Escherichia coli*, *E. fergussonii*, or a combination thereof. In certain embodiments the bacterium may be one which expresses the cutC/D gene cluster. The disclosure further provides a method of identifying a compound or extract that inhibits TMA production. The method comprises contacting a bacterium, such as a bacterium that is part of the gut microflora, or a bacterial lysate that metabolizes choline to produce TMA with a candidate composition, such as a composition comprising an extract of *Mikania* and detecting TMA (or a metabolite thereof). In certain embodiments, the level of TMA (or metabolite thereof) produced by the bacterium in contact with the candidate composition or bacterial lysate is compared to (a) the level of TMA produced by a bacterium or bacterial lysate not contacted with a composition or known inhibitor of TMA production, or (b) the level of TMA produced by the bacterium or bacterial lysate prior to contact with the candidate composition. A reduction in the level of TMA produced by the bacterium or bacterial lysate indicates that the candidate composition inhibits conversion of choline to TMA.

A method of inhibiting the conversion of choline to TMA in vitro also is contemplated. The method comprises contacting bacteria or a bacterial lysate with one or more compositions comprising an extract of *Mikania*. In various embodiments, the bacteria comprises a single bacterial species or strain, or comprises a mixture of two or more (for example three, four, five, or more) different bacterial species or bacterial strains. Similarly, a bacterial lysate may be produced from a single bacterial species or strain, or a mixture of two or more (for example three, four, five, or more, including fecal or other intestinal content derived polymicrobial collections, or polymicrobial collections from the oral cavity) different bacterial species or bacterial strains.

It will be appreciated that "inhibiting conversion of choline to TMA" does not require complete elimination of TMA production via choline metabolism. Any reduction in TMA formation from choline or a choline related metabolite as a precursor is contemplated, e.g., at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% reduction; and also including from about 1% to about 100%, from about 10% to about 90%, from about 20% to about 80%, from about 30% to about 70%, from about 40% to about 60%, and any combinations thereof.

In various embodiments, the inhibition of conversion of choline to TMA by the compositions comprising an extract of *Mikania* is not brought about by an antibiotic mechanism of action, for example it is not brought about by an antibacterial mechanism of action, or by a mechanism of action which reduces cell viability to 10% or lower, when compared to vehicle control.

In various embodiments, the inhibition of conversion of choline to TMA by the compositions comprising an extract of *Mikania* is not brought about by a direct anti-inflammatory mechanism of action.

In one embodiment of the invention, the amount of composition or extract of *Mikania* needed to provide 50% inhibition of conversion of choline to TMA is less than the amount of composition or extract of *Mikania* that reduces cell viability to 10% or lower, when compared to vehicle control.

Any suitable method for measuring TMA in vitro or in vivo can be used in the context of the invention. TMA, metabolites of TMA (including TMAO, DMA, or MMA), stable isotopes of TMA (such as deuterium labeled TMA, such as d3-, d6-, or d9-TMA), stable isotopes of TMAO (such as deuterium labeled TMAO, such as d3-, d6-, or d9-TMAO), stable isotopes of DMA (such as deuterium labeled DMA, such as d3-, or d6-DMA), stable isotopes of MMA (such as deuterium labeled MMA, such as d3-MMA), or choline (including stable isotopes of choline, for example d9-choline) can be assessed quantitatively or qualitatively. Exemplary methods of detecting and quantifying TMA are described in, for example U.S. Pub. No. 2010/00285517, the disclosure of which is incorporated herein by reference in its entirety. For example, levels of TMA (or trimethylamine N-oxide (TMAO), DMA, or MMA) or choline are optionally measured via mass spectrometry, ultraviolet spectroscopy, or nuclear magnetic resonance spectroscopy. Mass spectrometers include an ionizing source (such as electrospray ionization), an analyzer to separate the ions formed in the ionization source according to their mass-to-charge (m/z) ratios, and a detector for the charged ions. In tandem mass spectrometry, two or more analyzers are included. Such methods are standard in the art and include, for example, HPLC with on-line electrospray ionization (ESI) and tandem mass spectrometry.

In various embodiments, TMA or TMAO is measured in a biological sample from an individual. Biological samples include, but are not limited to, whole blood, plasma, serum, urine, feces, saliva, sweat, vaginal fluid, gingival crevicular fluid, or tissue. The sample may be collected using any clinically-acceptable practice and, if desired, diluted in an appropriate buffer solution, heparinized, concentrated, or fractionated. Any of a number of aqueous buffer solutions at physiological pH, such as phosphate, Tris, or the like, can be used. Acidified buffers also may be used. For example, the final pH after adding buffer to sample may optionally be between pH 1 and pH 6, or between pH 1.5 and pH 3.0.

In addition, levels of TMA (or a metabolite or stable isotope thereof) or choline in the biological sample may be compared to a control value. The control value utilized will depend on the embodiment of the invention. In certain embodiments, the control value may be the level of TMA or TMAO produced in the individual (or by the bacterium) prior to administration or exposure to a composition comprising an extract of *Mikania*. In addition, the control value may be based on levels measured in comparable samples obtained from a reference group, such as a group of individuals from the general population, individuals diagnosed with a cardiovascular disease or other TMA-associated condition, individuals not previously diagnosed with a TMA-associated condition, nonsmokers, and the like, who have not been exposed to a composition comprising an extract of *Mikania*. Levels of TMA or TMAO or choline may be compared to a single control value or to a range of control values. An individual is optionally identified as having an enhanced level of TMA prior to administration by comparing the amount of TMA in a biological sample from the individual with a control value.

The invention further provides a method of improving cardiovascular health of an individual. The method comprises administering to the individual a composition comprising an extract of *Mikania*, as described above under the subheading "Extracts," in an amount effective to improve cardiovascular health. Cardiovascular health is assessed by testing arterial elasticity, blood pressure, ankle/brachial index, electrocardiogram, ventricular ultrasound, platelet function (for example platelet aggregation), and blood/urine tests to measure, for example cholesterol, albumin excretion, C-reactive protein, TMAO, or plasma B-type peptide (BNP) concentration. In various aspects of the invention, administration of the composition comprising an extract of *Mikania* improves or maintains one or more of the assay outcomes within normal ranges. Normal ranges of outcomes of each test are known in the art. Improvement in cardiovascular health is, in some embodiments, marked by a reduction in circulating total cholesterol levels, reduction in circulating low density lipoproteins (LDLs), reduction in circulating triglycerides, reduction in circulating levels of TMAO, or reduction in blood pressure.

The invention also includes a method of improving a condition associated with conversion of choline to TMA in an individual in need thereof. The method comprises administering to an individual a composition comprising an extract of *Mikania*, in an amount effective to improve the condition. "Improving a condition" refers to any reduction in the severity or onset of symptoms associated with a disorder caused, at least in part, by TMA. One of ordinary skill in the art will appreciate that any degree of protection from, or amelioration of, a TMA-related disorder or symptom associated therewith is beneficial to an individual, such as a human. The quality of life of an individual is improved by reducing to any degree the severity of symptoms in an individual or delaying the appearance of symptoms. Accordingly, a method in one aspect is performed as soon as possible after it has been determined that an individual is at risk for developing a TMA-related disorder or as soon as possible after a TMA-related disorder is detected.

The condition associated with the conversion of choline to trimethylamine is, in various aspects of the invention, a cardiovascular disease, trimethylaminuria, reduced or impaired kidney function, kidney disease, chronic kidney disease, end-stage renal disease, trimethylaminuria, obesity, insulin resistance, diabetes mellitus, Alzheimer's disease, dementia, cognitive impairment, non-alcoholic steatohepatitis (NASH), increased levels of TMA by bacteria in the vagina leading to vaginal odor, or production of TMA by bacteria on the body leading to body odor, or production of TMA by bacteria in the mouth leading to bad breath or oral care biofilm development, or during pregnancy where the third trimester and post-partum period are associated with an increased risk of thrombosis, thus lowering TMA and TMAO levels may reduce this risk.

The term "cardiovascular disease" (CVD) is used in the art in reference to conditions affecting the heart, heart valves, and vasculature (such as arteries and veins) of the body and encompasses diseases and conditions including, but not limited to, arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), cerebrovascular disease, adverse ventricular remodeling, ventricular systolic dysfunction, ventricular diastolic dysfunction, cardiac dysfunction, ventricular arrhythmia, and the like.

A condition may be atherosclerosis. Atherosclerosis involves the formation of atheromatous plaques that lead to narrowing ("stenosis") of the vasculature, which can ultimately lead to partial or complete occlusion or rupture (aneurism) of the vessel, heart failure, aortic dissection, and ischemic events such as myocardial infarction and stroke. In various non-limiting embodiments, an inventive method inhibits, reduces, or reverses (in whole or in part) the onset or progression of atherosclerosis (for example reducing or preventing hardening or thickening of the arteries, plaque formation, endothelium damage, or arterial inflammation). It will be recognized that an improvement in a condition such as atherosclerosis may occur through multiple pathways. In one example, an improvement in the condition arises from the inhibition of conversion of choline to TMA in the gut of the host, and not from a localized anti-inflammatory mechanism in the host.

A condition may be trimethylaminuria. Trimethylaminuria (TMAU) is a condition characterized by an inability of individuals to convert TMA to TMAO, wherein affected individuals may have a fish-like body odor present in their urine, sweat or breath. Yamazaki et al. Life Sciences (2004) 74: 2739-2747. Such individuals may benefit from a reduction in metabolism of substrates including but not limited to choline, to TMA by bacteria in the gut. Individuals with TMAU or those wishing to reduce their levels of TMA and TMAO, may also consume activated charcoal or copper chlorophyllin, which act as sequestering agents, for example to make TMA unavailable to transfer into the blood stream of an individual. Such sequestering agents may adsorb TMA, which is then excreted from the digestive tract along with the sequestering agent.

The invention further provides the composition comprising an extract of *Mikania* for use in inhibiting the conversion of choline to TMA in vivo or in vitro, for improving or maintaining a condition associated with the conversion of choline to TMA; and use of the composition comprising an extract of *Mikania* for inhibiting the conversion of choline to TMA in vivo or in vitro, for improving or maintaining a condition associated with the conversion of choline to TMA. As described previously, the present invention is based, at least in part, on the discovery that extract of *Mikania* inhibit choline metabolism by gut microbiota resulting in reduction in the formation of TMA and trimethylamine N-oxide (TMAO). The disclosure provides compositions and methods that for example inhibit the conversion of choline to TMA in vitro and in vivo, improve or maintain cardiovascular, cerebrovascular, and peripherovascular health, and improve or prevent a condition associated with TMA and TMAO.

In various embodiments, administration of the composition comprising an extract of *Mikania* results in reduced TMA or TMAO levels, reduced total cholesterol levels, reduced LDL levels, increased HDL levels, reduced triglyceride levels, or normalized levels of other biomarkers associated with CVD (for example excreted albumin, C-reactive protein, or plasma B-type peptide (BNP)). In some embodiments, the composition comprising an extract of *Mikania* reduces the risk of cardiovascular disease, trimethylaminuria, reduced or impaired kidney function, kidney disease, chronic kidney disease, end-stage renal disease, insulin resistance, trimethylaminuria, obesity, diabetes mellitus, Alzheimer's disease, dementia, cognitive impairment, or non-alcoholic steatohepatitis (NASH) when administered to an individual.

Administration Regimens and Compositions

The amount of a composition comprising an extract of *Mikania* administered to the individual is sufficient to inhibit (in whole or in part) formation of TMA from choline. In various aspects of the disclosure, the amount improves cardiovascular health or achieves a beneficial biological response with respect to an unwanted condition associated with TMA (for instance the amount is sufficient to ameliorate, slow the progression, or prevent a condition (such as CVD)). The effect can be detected by, for example, an improvement in clinical condition, reduction in symptoms, or by any of the assays or clinical diagnostic tests described herein. The precise effective amount for an individual can depend upon the individual's body weight, size, and health; the nature and extent of the condition; and the composition or combination of agents selected for administration. In various aspects, the amount of composition administered to an individual is about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg. An effective amount may be administered to an individual as a single deployment of composition or as a divided dose (such as a single dose administered in multiple subunits contemporaneously or close in time). An amount of composition may be delivered one, two, or three times a day; one, two, or three times a week; or one, two, three, or four times a month. The compound may be delivered as a prodrug, which is converted to an active drug in vitro or in vivo.

A composition comprising the extract of *Mikania* is administered by any route that allows inhibition of choline conversion to TMA. A composition comprising the extract is, in various aspects of the invention, delivered to an individual parenterally (for example intravenously, intraperitoneally, intrapulmonary, subcutaneously or intramuscularly), intrathecally, topically, transdermally, rectally, orally, sublingually, nasally or by inhalation. In various embodiments, an extract or a composition comprising an extract is administered to the gastrointestinal tract via, such as by ingestion. Sustained or extended release formulations may also be employed to achieve a controlled release of the compound when in contact with body fluids in the gastrointestinal tract. Extended release formulations are known in the art, and typically include a polymer matrix of a biological degradable polymer, a water-soluble polymer, or a mixture of both, optionally with suitable surfactants.

The dosage form can comprise a polymer. Non-limiting examples of polymers can include hydrophilic polymers, water in-soluble polymers, acrylate copolymers, hypromellose acetate succinate, polyvinyl acetates and derivatives (commercially available as Kollicoat®, from BASF, Tarrytown, N.J.), shellac, polyvinyl alcohol, polyethylene glycol, and combinations thereof.

In one aspect, the polymer can be a hydrophilic polymer. Hydrophilic polymers can swell and dissolve slowly in aqueous acidic media, such as the stomach, thereby slowly releasing the actives in the stomach. However, pH increases when the dosage form reaches the intestines. The hydrophilic polymer can dissolve in a controlled quantity and extended release of the actives is achieved throughout the digestive tract.

Non-limiting examples of hydrophilic polymers can include natural or partially or totally synthetic hydrophilic gums such as acacia, gum tragacanth, locust bean gum, guar gum, or karaya gum, modified cellulosic substances such as ethylcellulose, cellulose acetate phthalate, carboxymethylcellulose (CMC) or a salt of CMC, hydroxypropylmethylcellulose (HPMC), hydroxypropyl cellulose, hydroxypropyl methylcellulose phthalate, hydroxypropyl methylcellulose acetate succinate, hydroxyethyl cellulose, cellulose acetate tetrahydrophthalate, cellulose acetate hexahydrophthalate, hydroxypropyl cellulose acetate succinate; proteinaceous substances such as agar, pectin, carrageen, and alginates; and other hydrophilic polymers such as carboxypolymethylene, gelatin, casein, zein, polysaccharides, modified starch derivatives, and combinations thereof.

In one example, the hydrophilic polymer can be HPMC, commercially available as METHOCEL™ ethers (available from Colorcon®, Harleysville, Pa.). In one example, the desired dissolution profile can be achieved using METHOCEL™ K100LV and/or METHOCEL™ K 100M.

In another aspect, the polymer can be a water-insoluble polymer. In one aspect, the water-insoluble polymers do not dissolve in solutions of a pH below 5 and thus do not dissolve in the low pH environment found in the gastric fluids of the stomach. Non-limiting examples of water-insoluble polymers can include polyacrylic acids, acrylic resins, acrylic latex dispersions, polyvinyl acetate phthalate, and other polymers common to those of skill in the art.

Non-limiting examples of acrylate copolymers can include methyl-methacrylate esters copolymerized with methacrylic acid, acrylic acid and esters copolymerized with methacrylic acid and esters, ammonia-containing acrylate copolymers, and combinations thereof.

In one aspect, the polymer can be an anionic copolymer based on methyl acrylate, methyl methacrylate, and methacrylic acid. In one aspect, the polymer can comprise Poly(methyl acrylate-co-methyl methacrylate-co-methacrylic acid) 7:3:1 polymer marketed under the tradename "Eudragit® FS30D", available from Evonik Industries, Darmstadt, Germany. In another aspect, the polymer can further comprise Poly(methacrylic acid-co-ethyl acrylate) 1:1 polymer, marketed under the tradename "Eudragit® L30D", commercially available from Evonik Industries, Darmstadt, Germany.

In one aspect, the polymer can be an extended release polymer. In one aspect, the extended release polymer can be a hydrophilic polymer such as HPMC.

In one aspect, the extended release portion can comprise a polymer. The extended release portion can comprise from about 10% to about 30% polymer, alternatively from about 15% to about 25% polymer, alternatively from about 18% to about 23% polymer, by weight of the portion. In another aspect, the extended release portion can comprise from about 25% to about 60% polymer, alternatively from about 30% to about 50% polymer, alternatively from about 35% to about 45%, alternatively from about 40% to about 50%, by weight of the portion.

In one aspect, the glass transition temperature (Tg) of the polymer can be relatively resistant to change upon exposure to water. The polymer can be exposed to water during processing from either tablet components or tableting pressures. An advantage of working with a polymer with a Tg that is relatively resistant to change is that the polymer is relatively rugged to water exposure during processing. Polymers that are mostly amorphous or partly amorphous can have a significant decrease in Tg with increasing water content, which means that additional care must be taken to protect against water exposure during processing or with incoming excipients to ensure that the polymer system does not decrease the Tg range during processing. Should this happen, manufacturing issues, such as hardness of the dosage forms, could be impacted.

The Tg takes place over a temperature range. Ti is the inflection temperature and Tf is the extrapolated onset temperature. The Ti for the polymer at about 75% relative humidity can be greater than about 25° C., alternatively greater than about 40° C., alternatively greater than about 60° C., alternatively greater than about 80° C., alternatively greater than about 90° C., alternatively greater than about 100° C., alternatively greater than about 110° C., alternatively greater than about 115° C., alternatively greater than about 120° C., as determined by the Glass Transition Temperature Test Method described hereafter. In another aspect, the Ti for the polymer at about 75% relative humidity can be from about 40° C. to about 175° C., alternatively from about 60° C. to about 160° C., alternatively from about 90° C. to about 155° C., alternatively from about 100° C. to about 150° C., alternatively from about 110° C. to about 148° C., alternatively from about 120° C. to about 145° C., alternatively from about 122° C. to about 139° C., as determined by the Glass Transition Temperature Test Method described hereafter.

The glass transition temperature can be determined using the following method. First, a 4-5 mg sample of polymer can be transferred into a standard open aluminum sample pan, available from DSC Consumables Inc. (Austin, Minn.). The open pan can equilibrate for several days inside a chamber that is controlled at 75% relative humidity. After the sample is equilibrated, the sample pan can be hermetically sealed and ASTM Method E1356-08 (Apr. 30, 2013) and can be run on a High Sensitivity Differential Scanning calorimeter, such as the Seiko X-DSC7000 available from Seiko Instruments Inc., per ASTM method E1356-08 over a temperature range of 5° C. to 250° C. The Ti and Tf can be determined as per the ASTM method.

In one aspect, the polymer can be a hypromellose and can have a viscosity from about 80 cP to about 250,000 cP, alternatively from about 100 cP to about 150,000 cP, alternatively from about 25,000 cP to about 100,000 cP, alternatively from about 50,000 cP to about 80,000 cP, as measured by 35 United States Pharmacopeia (USP) <911> (official from Dec. 1, 2012) and following the method for hypromellose samples having a viscosity type of greater than 600 mPa·s.

In one aspect, from about 50% to about 90% of the polymer particles can be between 106 μm and 212 μm, alternatively from about 60% to about 80%, alternatively from about 70% to about 80%, alternatively from about 72% to about 77%. In another aspect, greater than 75% of the polymer particles can be smaller than 212 μm, alternatively greater than 85%, alternatively greater than 90%, alternatively greater than 95%, alternatively greater than 97%. The polymer particle size distributions can be determined using 35 USP <786> Particle Size Distribution Estimation by Analytical Sieving (official from Dec. 1, 2012) and by using the mechanical agitation for dry sieving method. The particle size can affect the behavior of the formulation during processing, the compressibility of the formulation, and/or the uniformity of the final product.

In one aspect, the immediate release portion can comprise from about 15% to about 50% of a monosaccharide and/or a disaccharide by weight of the immediate release portion, alternatively from about 25% to about 40%, alternatively from about 30% to about 38%. In another aspect, the immediate release portion can comprise greater than about 20% of a soluble excipient, alternatively greater than about 25% by weight of the immediate release layer, alternatively greater than about 30%, alternatively greater than about 33%. In another aspect, the immediate release portion can comprise less than about 50% of a swellable excipient, which includes swellable polymers, by weight of the immediate release portion, alternatively less than about 40%, alternatively less than about 25%, alternatively less than about 20%, alternatively less than about 16%.

The invention provides an extract of *Mikania* or a composition comprising an extract of *Mikania* formulated with one or more physiologically acceptable excipients, carriers, stabilizers, tableting agents or diluent for use in the methods described herein. Excipients include, but are not limited to, carrier molecules that include large, slowly metabolized macromolecules such as proteins, polysaccharides, polylactic acids, polyglycolic acids, polymeric amino acids, amino acid copolymers, antioxidants (for example ascorbic acid), chelating agents (for example EDTA), carbohydrates (for example dextrin, hydroxyalkylcellulose, or hydroxyalkylmethylcellulose), liposomes, stearic acid, liquids (for example oils, water, saline, glycerol or ethanol), wetting or emulsifying agents, pH buffering substances, binders, disintegrants, flow agents, lubricants, fillers and the like.

The dosage forms can comprise additional excipients, including, but not limited to: lubricants such as microcrystalline cellulose, magnesium stearate, calcium stearate, zinc stearate, powdered stearic acid, hydrogenated vegetable oils, polyethylene glycol, and mineral oil; colorants; binders such as sucrose, lactose, starch paste, povidone and corn syrup; glidants such as colloidal silicon dioxide and talc; surface active agents such as sodium lauryl sulfate, dioctyl sodium sulfosuccinate, tricthanolamine, polyoxyetiylene sorbitan, poloxalkol, and quarternary ammonium salts; preservatives and stabilizers; sweeteners such as lactose, mannitol, glucose, fructose, xylose, galactose, maltose, xylitol, and sorbitol; xanthan gum; and alginic acid.

Examples of a dose or a dosage form include:

(i) an immediate release capsule comprising a gelatin capsule or an immediate release hydroxypropylmethylcellulose (HPMC) capsule, 1 μg to 500 mg of an extract of *Mikania*, 10%-99% of a filler, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, wherein the composition is optionally processed by a wet or dry granulation step with a suitable binding agent prior to encapsulation;

(ii) an immediate release tablet comprising 1 μg to 500 mg of an extract of *Mikania*, 10%-99% of a filler or binding agent, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, wherein the composition is optionally processed by a wet or dry granulation step with a suitable binding agent prior to tableting;

(iii) a sustained release capsule comprising a DRcaps™ capsule (Capsugel, USA), gelatin capsule or an immediate release hydroxypropylmethylcellulose (HPMC) capsule, 1 μg to 500 mg of an extract of *Mikania*, 10% to 60% of a sustained release excipient, for example K100M HPMC, 10%-70% of a filler or binding agent, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, and wherein the composition is optionally processed by a wet or dry granulation step with a suitable binding agent prior to encapsulation;

(iv) a sustained release tablet comprising 1 μg to 500 mg of an extract of *Mikania*, 10% to 60% of a sustained release excipient, for example K100M HPMC, 10%-70% of a filler or binding agent, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, and wherein the composition is optionally processed by a wet or dry granulation step with a suitable binding agent prior to encapsulation;

(v) a pseudo enteric capsule comprising a DRcaps™ capsule (Capsugel, USA), gelatin capsule or immediate release HPMC capsule, 1 μg to 500 mg of an extract of *Mikania*, 10%-60% of a filler, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, wherein the composition is optionally processed by a wet or dry granulation step with a suitable binding agent prior to encapsulation, and the capsule is optionally coated with a pseudo enteric option including a combination of Colorcon® Opadry® Clear YS-1-19025-A (Colorcon, USA) and Colorcon® Nutrateric.® (Colorcon, USA); and, (vi) a pseudo enteric tablet (with or without sustained release) comprising 1 μg to 500 mg of an extract of *Mikania*, 10-99% filler or binding agent, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, wherein the composition is optionally processed by a wet or dry granulation step with a suitable binding agent prior to tableting, and the tablet is coated with a pseudo enteric option including a combination of Colorcon® Opadry® Clear YS-1-19025-A (Colorcon, USA) and Colorcon® Nutrateric.® (Colorcon, USA).

(vii) an immediate release capsule comprising a gelatin capsule or an immediate release hydroxypropylmethylcellulose (HPMC) capsule, 0.1 μg to 50 mg of (2-hydroxyethyl) dimethylsulfonium, 10%-99% of a filler, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, wherein the composition is optionally processed by a wet or dry granulation step with a suitable binding agent prior to encapsulation;

(viii) an immediate release tablet comprising 0.1 μg to 50 mg of (2-hydroxyethyl) dimethylsulfonium, 10%-99% of a filler or binding agent, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, wherein the composition is optionally processed by a wet or dry granulation step with a suitable binding agent prior to tableting;

(ix) a sustained release capsule comprising a DRcaps™ capsule (Capsugel, USA), gelatin capsule or an immediate release hydroxypropylmethylcellulose (HPMC) capsule, 0.1 µg to 50 mg of (2-hydroxyethyl) dimethylsulfonium, 10% to 60% of a sustained release excipient, for example K100M HPMC, 10%-70% of a filler or binding agent, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, and wherein the composition is optionally processed by a wet or dry granulation step with a suitable binding agent prior to encapsulation;

(x) a sustained release tablet comprising 0.1 µg to 50 mg of (2-hydroxyethyl) dimethylsulfonium, 10% to 60% of a sustained release excipient, for example K100M HPMC, 10%-70% of a filler or binding agent, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, and wherein the composition is optionally processed by a wet or dry granulation step with a suitable binding agent prior to encapsulation;

(xi) a pseudo enteric capsule comprising a DRcaps™ capsule (Capsugel, USA), gelatin capsule or immediate release HPMC capsule, 0.1 µg to 50 mg of (2-hydroxyethyl) dimethylsulfonium, 10%-60% of a filler, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, wherein the composition is optionally processed by a wet or dry granulation step with a suitable binding agent prior to encapsulation, and the capsule is optionally coated with a pseudo enteric option including a combination of Colorcon® Opadry® Clear YS-1-19025-A (Colorcon, USA) and Colorcon® Nutrateric.® (Colorcon, USA); and, (xii) a pseudo enteric tablet (with or without sustained release) comprising 0.1 µg to 50 mg of (2-hydroxyethyl) dimethylsulfonium, 10-99% filler or binding agent, for example lactose, microcrystalline cellulose, maltodextrin or sucrose, up to 1% of a lubricant, for example magnesium stearate, sodium stearyl fumarate or stearic acid, up to 5% of a flow agent, for example silicon dioxide or talc, optionally a disintegrant, wherein the composition is optionally processed by a wet or dry granulation step with a suitable binding agent prior to tableting, and the tablet is coated with a pseudo enteric option including a combination of Colorcon® Opadry® Clear YS-1-19025-A (Colorcon, USA) and Colorcon® Nutrateric.® (Colorcon, USA).

Compositions, such as for parenteral or oral administration, are typically solids (for example, a lyophilized powder or cake), liquid solutions, emulsions or suspensions, while inhalable compositions for pulmonary administration are generally liquids or powders. Exemplary dosage forms include, but are not limited to, tablets, troches, lozenges, aqueous or oil suspensions, non-aqueous solutions, powders, dispersible powders or granules (including micronized particles or nanoparticles), emulsions, hard or soft capsules, hard or soft liquid-filled capsules, gelcaps, syrups, and elixirs. Solid dose compositions, for example tablets or liquid filled capsules may be uncoated or may be coated by known techniques including microencapsulation to delay disintegration and adsorption in the gastrointestinal or digestive tract. Solid dose compositions may be coated to target delivery to a specific region of the digestive tract. For example, the composition may be enteric coated to target delivery of the composition to the small intestine, the large intestine, or to the colon. Additional exemplary dosage forms may comprise coated microcapsules or coated microbeads in a suspension or liquid chassis. In some embodiments, the composition is delivered in a liquid dose, for example as a beverage, an infusion or tincture in water or alcohol, an infusion such as a tea following infusion of the composition in hot water or near boiling water. In some embodiments, the compositions comprising an extract of *Mikania* is provided as a dietary (for example food or drink) supplement. Dietary supplements are orally dosed and typically comprise vitamins, minerals, herbs or other botanicals, amino acids, enzymes, organ tissues, tissues from glands, or metabolites. For example, a composition comprising an extract of *Mikania* may be provided as a food in the form of a bar.

In some embodiments, the extract or composition described herein may be formulated for oral administration in a lipid-based composition suitable for low solubility materials and extracts. Lipid-based compositions can generally enhance the oral bioavailability of such materials and extracts. As such, the composition comprises in some aspects, an amount of an extract described herein together with at least one excipient selected from medium chain fatty acids and propylene glycol esters thereof (e.g., propylene glycol esters of edible fatty acids, such as caprylic and capric fatty acids) and physiologically acceptable surfactants, such as polyoxyl 40 hydrogenated castor oil.

In some embodiments, the extract or composition described herein may be provided in a delayed release composition, and optionally be released in a specific region of the digestive tract of an individual. For example, the extracts or composition may be provided such that the extract or composition is released from an orally dosed composition in the distal portion of the digestive tract such as the ileum or the colon. In certain embodiments, the delayed release composition releases the extract or composition at a specific pH, or at a range of pH for targeted delivery within the digestive tract of an individual. The extracts or compositions may be released, for example, between pH 6.0 and pH 9.0, between pH 6.5 and pH 8.0, between pH 6.5 and pH 7.5, between pH 7.0 and pH 7.5, or between pH 7.0 and pH 8.0.

A method of the invention may comprise administering a second agent to an individual. The term "second agent" merely serves to distinguish the agent from the extract of *Mikania* or compositions comprising an extract of *Mikania* and is not meant to limit the number of additional agents used in a method or denote an order of administration. One or more second agents are optionally incorporated in the composition with the extract of *Mikania* administered concurrently but in separate dosage forms or administered separately in time.

Exemplary second agents include, but are not limited to, antimicrobials (such as antibiotics that kill bacteria in the gut); agents that improve intestinal motility (such as fiber or psyllium); agents that further reduce TMA levels in the gut including sequestering agents (such as activated charcoal, or copper chlorphyllin); agents that further reduce TMA levels or production of TMA metabolites; agents that improve one or more aspects of cardiovascular health, such as agents that normalize blood pressure, decrease vascular inflammation, reduce platelet activation, normalize lipid abnormalities; agents that promote the excretion of TMA from the body; or agents that bind TMA so that it cannot be converted to TMAO. In various embodiments, the second agent is selected from the group consisting of Omega 3 oil, salicylic acid (aspirin), dimethylbutanol, garlic oil, garlic extract, olive oil, hill oil, Co enzyme Q-10, a probiotic, a prebiotic, a dietary fiber, psyllium husk, pistachio nuts, bismuth salts, phytosterols, grape seed oil, grape pomace, green tea extract, vitamin D, an antioxidant (such as vitamin C and vitamin E), turmeric, curcumin, resveratrol, red yeast rice, fermented forms of rice, fermented forms of soybean, lactofermented fruits and vegetables, including lactofermented apple puree, berberine, activated charcoal, or copper chlorophyllin. In certain embodiments, the composition comprises dimethylbutanol or inhibitors of the formation of TMA from precursors other than choline (for example betaine, phosphatidylcholine, crotonobetaine, or carnitine). Additional exemplary second agents are described in US 2017/0151208, US 2017/0151250, US 2017/0152222, US 2018/0000754, U.S. application Ser. No. 16/149,882, U.S. application Ser. No. 16/149,913, or U.S. application Ser. No. 16/149,938, which are incorporated here by reference.

A method of the disclosure may further comprise administration of one or more cardiovascular disease therapies. Examples of therapies include, but are not limited to, statins (e.g., Lipitor™ (atorvastatin), Pravachol™ (pravastatin), Zocor™ (simvastatin), Mevacor™ (lovastatin), and Lescol™ (fluvastatin)) or other agents that interfere with the activity of HMGCoA reductase, nicotinic acid (niacin, which lowers LDL cholesterol levels), fibrates (which lower blood triglyceride levels and include, for example Bezafibrate (such as Bezalip®), Ciprofibrate (such as Modalim®), Clofibrate, Gemfibrozil (such as Lopid®) and Fenofibrate (such as TriCor®)), bile acid resins (such as Cholestyramine, Colestipol (Colestid), and Cholsevelam (Welchol)), cholesterol absorption inhibitors (such as Ezetimibe (Zetia®, Ezetrol®, Ezemibe®)), phytosterols such as sitosterol (Take Control (Lipton)), sitostanol (Benechol), or stigmastanol), alginates and pectins, lecithin, and nutraceuticals (such as extract of green tea and other extracts that include polyphenols, particularly epigallocatechin gallate (EGCG), Cholest-Arrest™ (500 mg garlic and 200 mg lecithin), Cholestaway™ (700 mg Calcium carbonate, 170 mg magnesium oxidem 50 μg chromium picolinate), Cholest-Off™ (900 mg of plant sterols/stanols), Guggul Bolic (750 mg gugulipid (*Commiphora mukul* gum resin), and Kyolic® (600 mg aged garlic extract and 380 mg lecithin)).

In related variations of the preceding embodiments, a composition comprising an extract of *Mikania* described herein, alone or in combination with one or more second agents(s), may optionally be arranged in a kit or package or unit dose, such as a kit or package or unit dose permitting co-administration of multiple agents. In another aspect, the composition comprising an extract of *Mikania* and the one or more second agents are in admixture. In various embodiments, the component(s) of the kit or package or unit dose are packaged with instructions for administering the component(s) to an individual.

Other aspects and advantages of the present invention will be understood upon consideration of the following illustrative examples, which are not intended to be limiting in any way.

EXAMPLES

Example 1: Preparation of Extracts of *Mikania*

All extraction procedures were performed at room temperature (RT) and atmospheric pressure unless stated otherwise.

The following are exemplary methods that may be used to generate extracts from *Mikania* species.

Extraction from biological raw material powder.

Example source biological raw materials (BRM) used to derive extract of *Mikania* species are set forth in TABLE 1.

TABLE 1

| Extract ID | Genus/Species | Part of plant | Extraction method or final extraction solvent |
|---|---|---|---|
| 1 | *Mikania guaco* [a] | Leaf | 1:1 v/v water:ethanol |
| 2 | *Mikania guaco* [a] | Leaf | 1:1 v/v Hexane:ethyl acetate |
| 3 | *Mikania guaco* [a] | Leaf | Pellet 2 from Extract ID 2, extracted with Ethyl acetate |
| 4 | *Mikania guaco* [a] | Leaf | Pellet 3 from Extract ID 3, extracted with Ethanol |
| 5 | *Mikania guaco* [a] | Leaf | Pellet 4 from Extract ID 4, extracted with Water |
| 6 | *Mikania guaco* [a] | Leaf | Methanol |
| 7 | *Mikania guaco* [a] | Leaf | Water (RT) |
| 8 | *Mikania guaco* [a] | Leaf | Water (50° C.) |
| 9 | *Mikania guaco* [a] | Leaf | Water (100° C.) |
| 10 | *Mikania micrantha* [b] | Leaf | Methanol |
| 11 | *Mikania micrantha* [c] | Unknown | As received from supplier |
| 12 | *Mikania scandens* [d] | Unknown | As received from supplier |
| 13 | *Mikania guaco* [e] | Stem | Methanol |
| 14 | *Mikania guaco* [e] | Flower | Methanol |
| 15 | *Mikania guaco* [e] | Flower | Methanol |
| 16 | *Mikania grazielae* [e] | Stem | Methanol |
| 17 | *Mikania speciosa* [e] | Flower | Methanol |
| 18 | *Mikania sessilifolia* [e] | Leaf | Methanol |

[a] ChromaDex, Irvine CA, USA. Part number 00031379-506, guaco (*Mikania*) leaf. Supplied as a powder and referenced herein as biological raw material (BRM) powder.
[b] ChromaDex, Irvine CA, USA. Lot number is MM032719, *Mikania micrantha*. Supplied as dried leaf and stem, from which samples of leaf were isolated by hand and are referred to as BRM for this sample.
[c] PhytoPharmacon, Inc., Ganter, North Carolina, USA. Catalogue number BP2432. Supplied as a freeze-dried powder.
[d] PhytoPharmacon, Inc., Ganter, North Carolina, USA. Catalogue number BP2434. Supplied as a freeze-dried powder.
[e] Non-commercial sample.

Extract ID 1:

Two grams of biological raw material (BRM) powder in a 15 mL screw top polystyrene tube (15 mL Centrifuge Tube, EK-4021, AccuFlow Systems Inc, Maryland, USA) were suspended in 10 mL of 1:1 v/v water:ethanol (UltraPure™ DNase/RNase-Free Distilled Water, Cat #10977. Ethanol, 200 proof, EMD EX0276-3. Thermo Fisher Scientific, Massachusetts, USA) and vortexed (3200 rpm) for 15 minutes. The mixture was centrifuged at 800-1000×g for 15 minutes to generate Pellet 1 and Supernatant 1. Supernatant 1 was removed and divided into 1 mL aliquots in polypropylene microcentrifuge tubes then dried down with nitrogen sparging. All samples were stored at RT (room temperature) in a light resistant desiccator until use. The resulting dried pellet from Supernatant 1 was resuspended in 100 μL sterile water+0.1% v/v Triton X-100 (Invitrogen) to generate Extract ID 1 and vortexed as above. Serial dilutions of Extract ID 1, diluted in sterile water with 0.1% Triton X-100 were made based on an estimated starting concentration of 2 grams (g) of BRM/10 mL solvent. All samples were then stored at RT in a light resistant desiccator until use.

Extract ID 2:

Two grams of biological raw material (BRM) powder in a 15 mL screw top polystyrene tube (15 mL Centrifuge Tube, EK-4021, AccuFlow Systems Inc, Maryland, USA) were suspended in 10 mL of 1:1 v/v hexane/ethyl acetate (Hexanes, GR ACS, EMD HX0299-6; Ethyl acetate, anhydrous, 99.8%, Cat #270989-1L, Sigma Aldrich, Missouri, USA) and vortexed (3200 rpm) for 15 minutes. The mixture was centrifuged at 800-1000×g for 15 minutes to generate Pellet 2 and Supernatant 2. Supernatant 2 was removed and divided into 1 mL aliquots in polypropylene microcentrifuge tubes then dried down with nitrogen sparging. All samples were stored at RT in a light resistant desiccator until use. The resulting dried pellet from Supernatant 2 was resuspended in 100 µL sterile water+0.1% v/v Triton X-100 (Thermo Fisher) and vortexed as above, to generate Extract ID 2. Serial dilutions of Extract ID 2, diluted in sterile water with 0.1% v/v Triton X-100 were made based on an estimated starting concentration of 2 g BRM/10 mL solvent. All samples were then stored at RT in a light resistant desiccator until use.

Extract ID 3:

Pellet 2 in a 15 mL screw top polystyrene tube was resuspended in 10 mL ethyl acetate (Ethyl acetate, anhydrous, 99.8%, Cat #270989-1L, Sigma Aldrich) and vortexed (3200 rpm) for 15 minutes. The mixture was centrifuged at 800-1000×g for 15 minutes to generate Pellet 3 and Supernatant 3. Supernatant 3 was removed and divided into 1 mL aliquots in polypropylene microcentrifuge tubes, then dried down with nitrogen sparging. All samples were stored at RT in a light resistant desiccator until use. The resulting dried pellet from Supernatant 3 was resuspended in 100 µL sterile water+0.1% v/v Triton X-100 (Thermo Fisher) and vortexed as above, to generate Extract ID 3. Serial dilutions of Extract ID 3, diluted in sterile water with 0.1% v/v Triton X-100 were made based on an estimated starting concentration of 2 g BRM/10 mL solvent. All samples were then stored at RT in a light resistant desiccator until use.

Extract ID 4:

Pellet 3 in a 15 mL screw top polystyrene tube was resuspended in 10 mL ethanol (Ethanol, 200 proof, EMD EX0276-3) and vortexed (3200 rpm) for 15 minutes. The mixture was centrifuged at 800-1000×g for 15 minutes to generate Pellet 4 and Supernatant 4. Supernatant 4 was removed and divided into 1 mL aliquots in polypropylene microcentrifuge tubes, then dried down with nitrogen sparging. All samples were stored at RT in a light resistant desiccator until use. The resulting dried pellet from Supernatant 4 was resuspended in 100 µL sterile water+0.1% v/v Triton X-100 (Thermo Fisher) and vortexed as above, to generate Extract ID 4. Serial dilutions of Extract ID 4, diluted in sterile water with 0.1% v/v Triton X-100 were made based on an estimated starting concentration of 2 g BRM/10 mL solvent. All samples were then stored at RT in a light resistant desiccator until use.

Extract ID 5:

Pellet 4 in a 15 mL screw top polystyrene tube was resuspended in 10 mL water (UltraPure™ DNase/RNase-Free Distilled Water, Invitrogen Cat #10977) and vortexed (3200 rpm) for 15 minutes. The mixture was centrifuged at 800-1000×g for 15 minutes to generate Pellet 5 and Supernatant 5. Supernatant 5 was removed and divided into 1 mL aliquots in polypropylene microcentrifuge tubes, then dried down with nitrogen sparging. All samples were stored at RT in a light resistant desiccator until use. The resulting dried pellet from Supernatant 5 was resuspended in 100 µL sterile water+0.1% v/v Triton X-100 (Thermo Fisher) and vortexed as above, to generate Extract ID 5. Serial dilutions of Extract ID 5, diluted in sterile water with 0.1% v/v Triton X-100 were made based on an estimated starting concentration of 2 g BRM/10 mL solvent. All samples were stored at RT in a light resistant desiccator until use. All samples were then stored at RT in a light resistant desiccator until use.

Extract ID 6:

Half a gram (0.5 g) of biological raw material (BRM) powder in a 5 mL screw top polystyrene tube (5 mL Five-O™ Screw Cap MacroTubes™, MTC Bio Cat #C2540) was suspended in 2.5 mL of methanol (Methanol, ≥99.8% ACS, VWR BDH1135-4LG) and vortexed (3200 rpm) for 15 minutes. The mixture was centrifuged at 800-1000×g for 15 minutes to generate Pellet 6 and Supernatant 6. Supernatant 6 was removed and divided into 1 mL aliquots in polypropylene microcentrifuge tubes then dried down with nitrogen sparging. All samples were stored at RT in a light resistant desiccator until use. The resulting dried pellet from Supernatant 6 was resuspended in 100 µL sterile water+0.1% v/v Triton X-100 (Thermo Fisher) and vortexed as above, to generate Extract ID 6. Serial dilutions of Extract ID 6, diluted in sterile water with 0.1% v/v Triton X-100 were made based on an estimated starting concentration of 2 g BRM/10 mL solvent. All samples were then stored at RT in a light resistant desiccator until use.

Extract ID 7:

Half a gram (0.5 g) of biological raw material (BRM) powder in a 5 mL screw top polystyrene tube (5 mL Five-O™ Screw Cap MacroTubes™, MTC Bio Cat #C2540) was suspended in 2.5 mL of room temperature water (ultrapure water from MilliQ Advantage A10) and vortexed (3200 rpm) for 15 minutes. The mixture was centrifuged at 800-1000×g for 15 minutes to generate Pellet 7 and Supernatant 7. Supernatant 7 was removed and divided into 1 mL aliquots in polypropylene microcentrifuge tubes then dried down with nitrogen sparging. All samples were stored at RT in a light resistant desiccator until use. The resulting dried pellet from Supernatant 7 was resuspended in 100 µL sterile water+0.1% v/v Triton X-100 (Thermo Fisher) and vortexed as above, to generate Extract ID 7. Serial dilutions of Extract ID 7, diluted in sterile water with 0.1% v/v Triton X-100 were made based on an estimated starting concentration of 2 g BRM/10 mL solvent. All samples were then stored at RT in a light resistant desiccator until use.

Extract ID 8:

Half a gram (0.5 g) of biological raw material (BRM) powder in a 5 mL screw top polystyrene tube (5 mL Five-O™ Screw Cap MacroTubes™, MTC Bio Cat #C2540) was suspended in 2.5 mL of water at 50° C. (ultrapure water from MilliQ Advantage A10) and vortexed (3200 rpm at RT) for 15 minutes. The mixture was centrifuged at 800-1000×g for 15 minutes to generate Pellet 8 and Supernatant 8. Supernatant 8 was removed and divided into 1 mL aliquots in polypropylene microcentrifuge tubes then dried down with nitrogen sparging. All samples were stored at RT in a light resistant desiccator until use. The resulting dried pellet from Supernatant 8 was resuspended in 100 µL sterile water+0.1% v/v Triton X-100 (Thermo Fisher) and vortexed as above, to generate Extract ID 8. Serial dilutions of Extract ID 8, diluted in sterile water with 0.1% v/v Triton X-100 were made based on an estimated starting concentration of 2 g BRM/10 mL solvent. All samples were then stored at RT in a light resistant desiccator until use.

Extract ID 9:

Half a gram (0.5 g) of biological raw material (BRM) powder in a 5 mL screw top polystyrene tube (5 mL Five-O™ Screw Cap MacroTubes™, MTC Bio Cat #C2540) was suspended in 2.5 mL of water at 100° C. (ultrapure water from MilliQ Advantage A10) and vortexed (3200 rpm at RT) for 15 minutes. The mixture was centrifuged at 800-1000×g for 15 minutes to generate Pellet 9 and Supernatant 9. Supernatant 9 was removed and divided into 1 mL aliquots in polypropylene microcentrifuge tubes then dried down with nitrogen sparging. All samples were stored at RT in a light resistant desiccator until use. The resulting dried pellet from Supernatant 9 was resuspended in 100 µL sterile water+0.1% v/v Triton X-100 (Thermo Fisher) and vortexed as above, to generate Extract ID 9. Serial dilutions of Extract ID 9, diluted in (solvent—water with 0.1% v/v Triton X-100) were made based on an estimated starting concentration of 2 g BRM/10 mL solvent. All samples were then stored at RT in a light resistant desiccator until use.

Extract ID 10:

The sample was received from the supplier as dried leaf and stem. Leaf pieces were isolated by hand and then prepared as described for Extract ID 6.

Extract ID 11:

The sample was received from the supplier as 10 mg dried extract per well in a 96 well plate. The sample was resuspended in DMSO to a concentration of 10 mg/mL with pipetting to mix.

Extract ID 12:

The sample was received from the supplier as 10 mg dried extract per well in a 96 well plate. The sample was resuspended in DMSO to a concentration of 10 mg/mL with pipetting to mix.

Extract ID 13 Through 18:

Samples were received as biological raw material and processed as described for Extract ID 6.

Example 2: Assay for Identifying and Characterizing Extracts that Inhibit the Formation of TMA from Choline This example provides an exemplary assay for identifying and characterizing extracts of *Mikania* that inhibit the formation of TMA from choline.

*Proteus mirabilis* 29906 (Pm) strain was grown aerobically overnight in 500 ml of Nutrient Broth media (3 g/L beef extract, 5 g/L Peptone; Difco #234000) at 37° C. with 250 rpm shaking. The biomass was pelleted by centrifugation at 6000×g for 12 minutes at 4° C. The cell pellet was suspended in 240 mL of ice-cold 1× Phosphate Buffered Saline ($Ca^{2+}$ and $Mg^{2+}$ free). Ninety micrograms of Lysozyme (Sigma #L6876 Lot #SLBG8654V; Sigma-Aldrich Corp., St. Louis, Mo.) was added and incubated with 320 rpm shaking for 30 minutes at 4° C. Lysis was achieved via French press with a 4° C. prechilled 1" diameter chamber at 1000 psi (high ratio; internal PSI equivalent ~16000). The lysate was centrifuged at 6,000×g for 12 minutes at 4° C. to pellet extra debris. A protein concentration of the centrifuged lysate supernatant was determined by a BCA Protein Assay Kit (Pierce #23225; Thermo Fisher Scientific Co., Waltham, Mass.) and protein concentration adjusted to 3 mg/ml with 1× Dulbecco's phosphate buffered saline (DPBS). The centrifuged supernatant lysate was aliquoted into 20 mL volumes and stored frozen at −80° C.

*Proteus mirabilis* 29906 (Pm) lysate was diluted to 1.5 mg/mL protein with 1×DPBS. Choline chloride (CC) (1M stock) was added to reach a final concentration of 2.5 mM choline chloride. The mixture was mixed using a vortex mixer for approximately 15 seconds and incubated at 37° C. for 22 hours. After incubation, 150 µL of CC-treated Pm lysate was dispensed into a deep-well plate (polypropylene, 2 mL volume, Corning Axygen catalogue #P-DW-20-C). Candidate extracts from TABLE 1 and vehicle control (respective vehicle control of sterile water with 0.1% v/v Triton X-100, DMSO or water), or control compounds ($IC_{50}$ control, 8-Quinolinol hemisulfate salt (Sigma Catalog #55100)) were added at a 1:100 dilution (e.g., 1.5 µL per well). The plates were agitated on a plate shaker for 1 minute. d9-choline chloride (1.5 µL of 5 mM, Cambridge Isotope Laboratories, Inc., USA, choline chloride (trimethyl-D9, 98%), catalog #DLM-549) was added to all wells to reach a final d9-choline chloride concentration of 50 µM.

The plates were again agitated on a plate shaker for 1 minute and incubated at 37° C. for two hours. After incubation, 1.5 µL of formic acid was added to each well (final concentration=1% formic acid). The plates were agitated on a plate shaker for 1 minute and placed on ice. Cell lysate samples were spiked with stable isotope labeled internal standard (22.5 µL of 6 µg/mL of 13C3-trimethylamine (13C3-TMA) was added to each sample), then d9-trimethylamine (d9-TMA), trimethylamine (TMA) and 13C3-TMA were isolated from the lysate after protein precipitation as described below. Acetonitrile acidified with 0.1% formic acid, 600 µL, was added to each sample which was then centrifuged (2,100 g for 20 minutes) to pellet the protein and other precipitates. The supernatant was removed and analyzed as described below. The TMA, d9-TMA and 13C3-TMA in the isolated supernatant samples were subjected to gradient High Performance Liquid Chromatography (HPLC) analysis on a Waters Atlantis HILIC Silica column, from Waters Corp., Milford, Mass., (2.1×50 mm, 3 µm particles) with an Atlantis Silica HILIC Sentry guard column, from Waters Corp., Milford, Mass., (100 Å, 3 µm, 2.1 mm×10 mm), 10 mM ammonium formate in water with 0.1% formic acid as mobile phase A and 0.1% formic acid in acetonitrile as mobile phase B. Detection and quantitation was achieved by tandem mass spectrometry operating under multiple reaction monitoring (MRM) MS/MS conditions (m/z 60.1→44.1 for TMA, m/z 69.1→49.1 for d9-TMA, m/z 63.0→46.1 for 13C3-TMA). TMA and d9-TMA calibration standards (STD), prepared in 80/20/0.1% acetonitrile/Water/Formic Acid, were used to construct a regression curve by plotting the response (peak area TMA/peak area 13C3-TMA) versus concentration for each standard. The concentrations of TMA and d9-TMA in the cell lysate were determined by interpolation from the quadratic (1/x2) regression curve.

EXAMPLE 2 provides exemplary methods of identifying and quantitating TMA in a sample, as well as screening candidate inhibitory extracts or compositions.

$IC_{50}$ measurements for inhibition of conversion of choline to TMA, as outlined in EXAMPLE 2, for representative extracts of *Mikania* from TABLE 1 are set forth in TABLE 2.

TABLE 2

| Extract ID | Extract source | $IC_{50}$ (Log g/mL) extract |
|---|---|---|
| 1 | *Mikania guaco*, leaf, Extract ID 1 | −5.91 |
| 2 | *Mikania guaco*, leaf, Extract ID 2 | >−3.00 |
| 3 | *Mikania guaco*, leaf, Extract ID 3 | −3.81 |
| 4 | *Mikania guaco*, leaf, Extract ID 4 | −4.53 |
| 5 | *Mikania guaco*, leaf, Extract ID 5 | −5.23 |
| 6 | *Mikania guaco*, leaf, Extract ID 6 | −5.71 |
| 7 | *Mikania guaco*, leaf, Extract ID 7 | >−3.00 |
| 8 | *Mikania guaco*, leaf, Extract ID 8 | −4.44 |
| 9 | *Mikania guaco*, leaf, Extract ID 9 | >−3.00 |
| 10 | *Mikania micrantha*, leaf, Extract ID 10 | >−3.00 |
| 11 | *Mikania micrantha*, Extract ID 11 | >−3.00 |
| 12 | *Mikania scandens*, Extract ID 12 | >−3.00 |
| 13 | *Mikania guaco*, stem, Extract ID 13 | −5.01 |

TABLE 2-continued

| Extract ID | Extract source | IC$_{50}$ (Log g/mL) extract |
|---|---|---|
| 14 | *Mikania guaco*, flower, Extract ID 14 | −6.39 |
| 15 | *Mikania guaco*, flower, Extract ID 15 | −5.89 |
| 16 | *Mikania grazielae*, stem, Extract ID 16 | −5.31 |
| 17 | *Mikania speciosa*, flower, Extract ID 17 | −5.83 |
| 18 | *Mikania sessilifolia*, leaf, Extract ID 18 | −3.10 |

Example 3 Polymicrobial Screening Method

Human fecal polymicrobial incubation with deuterium labeled choline extract screening method, including cell viability assay. All materials were pre-reduced in an anaerobic chamber for 24 hours before using in the experiments and experimental procedures were performed under anaerobic conditions (chamber purged with 85% nitrogen, 5% hydrogen, 10% carbon dioxide).

Human fecal samples were collected from a healthy male volunteer with no chronic illnesses, blood borne diseases or active infections. The volunteer had not received antibiotics within two months prior to donation and provided written informed consent. Samples were diluted to make a 20% (w/v) fecal slurry by resuspension of the feces in a media containing 3% (w/v) tryptic soy broth, 1% (w/v) trehalose, pH 7.3. The fecal slurry was homogenized and filtered by hand using a stomacher bag with an integrated 170 µm membrane. DMSO (5% (w/v)) was added to the filtered slurry and aliquots were stored in cryogenic vials at −80° C. until use. Frozen fecal slurries were diluted to 0.2% (w/v) with M9 media (Na$_2$HPO$_4$ (6 g/L), KH$_2$PO$_4$ (3 g/L), NaCl (0.5 g/L) with addition of 0.1 mM CaCl$_2$) and 1 mM MgSO$_4$) and dispensed (1 mL) into deep well 96-well plates. Diluted fecal slurries containing 50 µM d9-choline chloride and compounds in doses ranging from equivalent 2 mg/mL to 31 ng/mL were sealed and incubated at 37° C. with shaking. After 20 hours, an aliquot of the fecal polymicrobial community was analyzed for viability using PrestoBlue cell viability reagent (Thermo Fisher Scientific, USA) as described below. The reaction plates were subsequently centrifuged (4000×g at 4° C. for 12 min) to pellet fecal material and 150 µL aliquots were transferred and quenched with addition of formic acid to 1% (v/v). All fecal processing and polymicrobial assay steps were performed in an anaerobic environment. The products were determined by LC/MS/MS and IC$_{50}$ values were calculated as described previously for detection and analysis of TMA and d9-TMA in EXAMPLE 2.

IC$_{50}$ measurements for inhibition of conversion of choline to TMA, as outlined in EXAMPLE 3, for representative extracts of *Mikania* from TABLE 1 are set forth in TABLE 3.

TABLE 3

| Extract ID | Extract source | IC$_{50}$ (Log g/mL) extract |
|---|---|---|
| 1 | *Mikania guaco*, leaf, Extract ID 1 | −6.03 |
| 5 | *Mikania guaco*, leaf, Extract ID 5 | −5.99 |
| 16 | *Mikania grazielae* stem, Extract ID 16 | −4.37 |
| 18 | *Mikania sessilifolia* leaf, Extract ID 18 | −3.74 |

EXAMPLE 3 provides exemplary methods of screening candidate inhibitory extracts or compositions for the conversion of choline to TMA.

For the PrestoBlue cell viability assay, a 6 µL aliquot of the fecal polymicrobial community assay was added to 84 µL M9 media in a black, clear bottom 96 well plate. To this was added 10 µL of PrestoBlue reagent, covered and shaken for 1 minute at 800 rpm. The plates were incubated at 37° C. for 30 minutes and fluorescence read following the manufacturer's instructions. Cell viability was calculated as % fluorescence compared to vehicle control (e.g. 1% DMSO).

TABLE 4 cell viability data as determined in EXAMPLE 3, with representative extracts of *Mikania*, in the PrestoBlue assay. Maximum concentration tested is reported, along with lowest concentration tested at which cell viability was determined to be 10% or lower, compared to vehicle control. If cell viability was not determined to be 10% or lower at any of the concentrations tested, the cell is marked N/A.

TABLE 4

| Extract ID | Extract source | Maximum Concentration Tested (mg/mL) | Lowest concentration tested at which cell viability was 10% or lower (mg/mL) |
|---|---|---|---|
| 1 | *Mikania guaco*, leaf, Extract ID 1 | 2 | N/A |
| 5 | *Mikania guaco*, leaf, Extract ID 5 | 2 | N/A |
| 16 | *Mikania grazielae* stem, Extract ID 16 | 0.1 | N/A |
| 18 | *Mikania sessilifolia* leaf, Extract ID 18 | 0.1 | N/A |

Example 4 Preclinical Screening Method

Starting at day 0, mice (C57bl/6, ~19 g, 10 wk of age; n=5/group) were maintained in accordance with the NIH guidelines in a 12:12 hr light:dark cycle and provided with 1% Choline Added diet (Envigo custom formulation prepared, similar to Teklad Global Rodent Diet 2018) ad libitum. Concurrent with introduction of the diet, mice were gavaged once daily orally using a 1.5" 22 G ball-tip curved feeding needle to administer compound in 200 µl or less of water at one or multiple of the dose 0, 1.0, 3.1, 10, 31, 100 or 310 mg/kg/day. Urine was collected once daily in the morning. Animals were restrained by hand and bladder was expressed by gentle palpation of the pelvic region. Aliquots of 1-5 µl of urine were centrifuged at 1,300×g for 5 min in a 1.5 mL conical bottom tube with a snap top, to precipitate any potential cellular debris, and supernatants were transferred to a clean screw-cap tube with o-ring seal and stored at −80° C. until analysis. Sixty microliters or less of blood was collected at 20 hours post gavage, into a heparinized capillary tube. Blood was kept at 4° C., then spun using a centrifuge (5 min in centrifuge designed to capillary tubes) to separate plasma and hematocrit within 4 hours after collection. Plasma samples were stored at −80° C.

Measurements of Choline Metabolites:

For measurement of TMA in plasma, samples were acidified (10 mM HCl final) prior to storage at −80° C. TMAO and trimethylamine (TMA) and their d9-isotopologues were quantified using stable isotope dilution HPLC with on-line electrospray ionization tandem mass spectrometry (LC/ESI/MS/MS) methods as described in (Wang Z, Klipfell E, Bennett B J, et al. (2011) Gut flora metabolism of phosphatidylcholine promotes cardiovascular disease. Nature 472: 57-63) using d4(1,1,2,2)-choline, d3(methyl)-TMAO, and d3(methyl)-TMA as internal standards. Concentrations of TMAO in urine were adjusted for urinary dilution by analysis of urine creatinine concentration. Samples were taken at different days during the studies and different doses were administered to avoid side effects at higher doses of some of the extracts or compositions.

EXAMPLE 4 provides exemplary methods of screening candidate inhibitory extracts or compositions for the conversion of choline to TMA and TMAO.

Example 5: Additional In Vitro Assay for Identifying and Characterizing Extracts or Compositions that Inhibit the Formation of TMA from Choline Ability of botanical extracts to inhibit the conversion of choline to TMA in cell lysates or whole cells were determined using methods as described in Wang, Z, Roberts, A B, Buffa J A, et al. (2015) Non-lethal inhibition of gut microbial trimethylamine production for the treatment of atherosclerosis, Cell 163: 1585-1595. Briefly, efficacy was measured as Log $IC_{50}$ (mg/mL) by inhibition of conversion of choline to TMA metabolized by recombinant *P. mirabilis* Cut C/D lysate; recombinant *D. alaskensis* Cut C/D lysate, or whole cell wild-type *P. mirabilis*.

EXAMPLE 5 provides exemplary methods of identifying and quantitating TMA in a sample, as well as screening candidate inhibitory extracts or compositions.

Example 6: Rapid Preclinical Method to Determine Compound Efficacy

Challenge: C57bl/6 female mice (8 wk of age ~20 g Body Weight) were maintained in accordance with the NIH guidelines in a 12:12 hr light:dark cycle on normal chow diet were placed in a clean cage without food ~1 hr prior to gavage.

Sample preparation: One mL aliquots each of Supernatant 5 (from EXAMPLE 1) were placed in polypropylene microcentrifuge tubes and dried down with nitrogen sparging (named Example 6 Dried Supernatant 5). All samples were stored at RT in a light resistant desiccator until use. This resulting dried pellet of Example 6 Dried Supernatant 5 was resuspended in 0.15 mL/tube ultra-pure water (named Example 6 Resuspended Supernatant 5). Four tubes of Example 6 Resuspended Supernatant 5 were combined to give 0.6 mL of material. Upon validation by mass spectrometry, the Example 6 Resuspended Supernatant 5 was found to be 0.6 g/mL. This 0.6 mL of material was combined 1:1 with 4.8 mg/mL d9-Choline. Each animal was given 0.2 mL of the Example 6 Resuspended Supernatant 5+d9-Choline mixture, or a 0.2 mL aliquot of dilutions thereof.

Mice were given 0.2 mL of the Example 6 Resuspended Supernatant 5+d9-Choline mixture (from above) or 0.2 mL of a 1/10, 1/100 or 1/1000 serial dilutions thereof, by oral gavage using a 1.5" 22 G ball-tip curved feeding needle to administer mixture. Food was returned after a 2 hr fast (1 hr after gavage administration). Blood (30 μL) was collected into a heparinized capillary tube at 1, 2, or 3 hours after gavage. Blood was kept at 4° C., then spun using a centrifuge (5 min in centrifuge designed to capillary tubes) to separate plasma and hematocrit within 4 hours after collection. Plasma samples were stored at −80° C. Concentration of d9 Choline, d9TMA and d9TMAO was measured by LC-MS/MS as described for EXAMPLE 4.

Flora Normalization: Twenty four hours post-gavage mice were placed in a clean cage and fecal material from conventional mice was spread in all the cages.

EXAMPLE 6 provides exemplary methods of screening candidate inhibitory extracts or compositions for the conversion of choline to TMA and TMAO.

$EC_{50}$ measurements (Concentration to provide 50% effective inhibition) for inhibition of plasma levels of TMAO, compared to vehicle control, as outlined in EXAMPLE 6, for representative extracts of *Mikania*, are set forth in TABLE 5.

TABLE 5: Calculated $EC_{50}$ (mg/Kg) for inhibition of TMAO production, compared to Vehicle Control, as described in EXAMPLE 6. The $EC_{50}$ is calculated at 3 hrs post-gavage.

TABLE 5

| Extract ID | Extract source | $EC_{50}$ (mg/Kg) extract |
|---|---|---|
| 1 | *Mikania guaco*, leaf, Extract ID 1 | 22.3 |

Example 7: Extraction and Identification of (2-hydroxyethyl) dimethylsulfoxonium Extraction and identification of (2-hydroxyethyl) dimethylsulfoxonium in *Mikania guaco* leaf was performed using bio-assay guided fractionation. Bioactivity was tested on partition and fraction samples to determine which samples needed further purification.

*Mikania guaco* leaf powder (ChromaDex, Irvine Calif., USA. Part number 00031379-506, guaco (*Mikania*) leaf) was extracted with methanol at a concentration of 100 mg/mL and stirred overnight. The sample was filtered to remove solid particulates and the extract was dried via a rotary evaporator to make EXTRACT ID 19. EXTRACT ID 19 was reconstituted in 4:1 v/v chloroform/methanol, at a concentration of 10 mg/mL. An equal volume of water was added to the solution and stirred for 5 min. The organic layer was removed to afford the desired aqueous partition, which was then dried in a rotary evaporator. The pellet from the aqueous partition was reconstituted in 1:1 v/v n-butanol/water at a concentration of 3 mg/mL. The aqueous partition was collected from this sample and dried to make EXTRACT ID 20.

EXTRACT ID 20 was brought up to 200 mg/mL in water and fractionated using preparative liquid chromatography. Initially, reverse-phase chromatography was performed using a C18 column (Waters, Atlantis T3, 5 μm, 19×250 mm) with a gradient from 0% to 20% methanol in water (0.1% formic acid) over 20 min at 13 mL/min. The first eluting peak at 4-5 min collected and dried in a rotary evaporator to make EXTRACT ID 21. EXTRACT ID 21 was brought up to 200 mg/mL in water and a second round of preparative liquid chromatography was performed, using a HILIC (YMC, Diol, 5 μm, 20×250 mm) column with A=90:10 v/v acetonitrile/water (10 mM ammonium formate) and B=water (10 mM ammonium formate). The gradient was from 90% to 65% mobile phase A over 25 min at 18 mL/min. A third round of preparative liquid chromatography was performed on the dried fraction which eluted at 6-8 min (at 80 mg/Ml resuspended in water), using the same HILIC column under isocratic conditions of 90:10 v/v acetonitrile/water (10 mM ammonium formate). The fraction which eluted at 13-14 minutes from this second round of HILIC, was collected and dried in a rotary evaporator, to make EXTRACT ID 22, and processed for identification.

Structural Identification

The structure of (2-hydroxyethyl) dimethylsulfoxonium in EXTRACT ID 22 was elucidated using HPLC-high resolution mass spectrometry (HRMS), tandem mass spectrometry (MS/MS), NMR (1H, 13C, and HSQC), and IR. The HRMS data provided the molecular formula of $C_4H_{11}O_2S^+$ and a prominent MS/MS fragment ion of $C_2H_7OS^+$. Thus, the presence of an ethoxylate functional group was supported. FT-IR supported the presence of the hydroxyl and sulfoxide functional groups. The HSQC NMR confirmed the proton/carbon correlations for the two distinct methylene groups and the two identical methyl groups. Additionally, the HRMS and NMR data matched data in the literature, reported for this structure (Warabi, K. et al. Comparative Biochemistry and Physiology Part B, 2001, 27-30), to further confirm the identification.

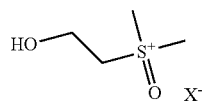

(2-hydroxyethyl) dimethylsulfoxonium, wherein X⁻ is chloride, bromide, iodide or a pharmaceutically acceptable anion.

Medium scale preparation of methanol extraction from *Mikania guaco* leaf.

Ten grams of *Mikania guaco* leaf powder (ChromaDex, Irvine Calif., USA. Part number 00031379-506, *guaco* (*Mikania*) leaf) in a 500 mL screw top polystyrene flask (Thermo Scientific) was suspended in 200 mL of methanol (VWR BDH BDH1135-4LG) and mixed for 1 hour. The mixture was centrifuged at 1000×g for 20 minutes to generate PELLET 23 and SUPERNATANT 23. SUPERNATANT 23 was removed and dried in a rotary evaporator with nitrogen sparging to generate EXTRACT ID 23. After the sample dried completely, the weight of EXTRACT ID 23 was calculated. All samples were stored at RT (room temperature) in a light resistant desiccator until use. An aliquot of EXTRACT ID 23 was resuspended to a stock concentration of 25 mg/mL using 0.1% v/v Triton X-100 (Sigma T8787), and vortexed as above. Serial dilutions of Extract ID 23 were diluted in sterile water with 0.1% Triton X-100, were made based on a high dose of 50 μg/mL. All samples were then stored at RT in a light resistant desiccator until use.

Inhibition of Conversion of Choline to TMA

For testing of inhibition of conversion of choline to TMA, EXTRACT ID 19, 20, 21, 22 or 23 (0.5 mg) were resuspended in 100 μL of 0.1% Triton X-100 in sterile water to a final concentration of 5 mg/mL. Serial dilutions of EXTRACT ID 19, 20, 21, 22 or 23 were prepared in 0.1% Triton X-100 in sterile water were made based on a high dose of 50 μg/mL.

Extracts IDs 19, 20, 21, 22 and 23 were tested according to the method of EXAMPLE 2 with serial dilutions in 0.1% Triton X-100 in sterile water. For EXTRACT IDs 19, 20, 21, 22, and 23 sample concentration was calculated based on actual mass of the material resuspended. The dosing range tested was from 50 μg/mL and 0.0031 μg/mL. Data are shown in TABLE 6.

TABLE 6

| Extract ID | Extract source | IC₅₀ (Log g/mL) extract |
|---|---|---|
| 19 | *Mikania guaco*, leaf, Extract ID 19 | −6.72 |
| 20 | *Mikania guaco*, leaf, Extract ID 20 | −7.09 |
| 21 | *Mikania guaco*, leaf, Extract ID 21 | −7.42 |
| 22 | *Mikania guaco*, leaf, Extract ID 22 | −8.59 |
| 23 | *Mikania guaco*, leaf, Extract ID 23 | −6.75 |

Extract IDs 20, 21, 22, and 23 were assayed according to EXAMPLE 3, as shown in TABLE 7 (inhibition of conversion of choline to TMA), and TABLE 8 (PrestoBlue viability data). For EXTRACT IDs 20, 21, 22 and 23, sample concentration was calculated based on actual mass of the material resuspended. The dosing range tested was from 50 μg/mL to 0.763 ng/mL.

TABLE 7

| Extract ID | Extract source | IC₅₀ (Log g/mL) extract |
|---|---|---|
| 20 | *Mikania guaco*, leaf, Extract ID 20 | −6.13 |
| 21 | *Mikania guaco*, leaf, Extract ID 21 | −6.66 |
| 22 | *Mikania guaco*, leaf, Extract ID 22 | −7.83 |
| 23 | *Mikania guaco*, leaf, Extract ID 23 | −5.79 |

TABLE 8

| Extract ID | Extract source | Maximum Concentration Tested (μg/mL) | Lowest concentration tested at which cell viability was 10% or lower (mg/mL) |
|---|---|---|---|
| 20 | *Mikania guaco*, leaf, Extract ID 20 | 50 | N/A |
| 21 | *Mikania guaco*, leaf, Extract ID 21 | 50 | N/A |
| 22 | *Mikania guaco*, leaf, Extract ID 22 | 50 | N/A |
| 23 | *Mikania guaco*, leaf, Extract ID 23 | 50 | N/A |

Example 8: Mass Spectrometry Method for Detection of (2-hydroxyethyl) dimethylsulfoxonium Methanol extracts of botanical material was prepared as described for Extract ID 6 and Extract ID 10 in EXAMPLE 1, except that following drying of the supernatant with nitrogen sparging, the resulting pellet was resuspended in water (UltraPure™ DNase/RNase-Free Distilled Water, Invitrogen Cat #10977) for detection of (2-hydroxyethyl) dimethylsulfoxonium.

Botanical extracts were diluted 100 to 500-fold with 0.1% formic acid in 80/20% acetonitrile/water and spiked with internal standard ($^{13}C_3$-trimethylamine ($^{13}C_3$-TMA)). Then (2-hydroxyethyl) dimethylsulfoxonium and $^{13}C_3$-TMA are subjected to gradient HPLC analysis on a Waters Atlantis HILIC Silica column (2.1×50 mm, 3 μm particles) with an Atlantis Silica HILIC Sentry guard column (100 Å, 3 μm, 2.1 mm×10 mm), 10 mM ammonium formate in water with 0.1% formic acid as mobile phase A and 0.1% formic acid in acetonitrile as mobile phase B. Detection and quantitation are by tandem mass spectrometry operating under multiple reaction monitoring (MRM) MS/MS conditions (m/z 123.0→79.0 for (2-hydroxyethyl) dimethylsulfoxonium, m/z 63.0→46.1 for $^{13}C_3$-TMA). (2-hydroxyethyl) dimethylsulfoxonium calibration standards (synthesized as described in EXAMPLE 9), prepared in 80/20/0.1% acetonitrile/Water/Formic Acid, are used to construct a regression curve by plotting the response (peak area (2-hydroxyethyl) dimethylsulfoxonium/peak area $^{13}C_3$-TMA) versus concentration for each standard. The concentrations of (2-hydroxyethyl) dimethylsulfoxonium in botanical extract are determined by interpolation from the quadratic $(1/x^2)$ regression curve.

TABLE 9

| Extract ID | Extract source | Starting concentration (mg BRM/mL MeOH) | (2-hydroxyethyl) dimethyl-sulfoxonium (ng/mL) |
|---|---|---|---|
| 6 | *Mikania guaco*, leaf | 25 | 122147 |
| 10 | *Mikania micrantha*, leaf | 25 | BQL |
| 13 | *Mikania guaco*, stem | 10 | 5025 |
| 14 | *Mikania guaco*, flower | 10 | 2776 |
| 15 | *Mikania guaco*, flower | 10 | 14648 |
| 16 | *Mikania grazielae*, stem | 25 | 4480 |
| 17 | *Mikania speciosa*, flower | 10 | 6919 |
| 18 | *Mikania sessilifolia*, leaf | Not Tested | |

BQL = Below Quantitation Limit (Limit of Quantitation in Sample: 10 ng/mL).

Example 9: Preparation of (2-hydroxyethyl) dimethylsulfoxonium

Synthesis was derived from the methods as described in Carle J. S., Christophersen, C. (1982) Toxicon 20:1, 307-310.

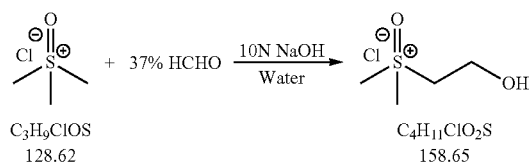

To a solution of trimethylsulfoxonium chloride (0.461 g, 3.585 mmol) and 37% HCHO (0.29 mL, 1 eq.) was added 10N NaOH (1.08 mL, 3 eq.) at RT. The resultant solution was stirred at RT for 15 min. The solution was neutralized by conc. HCl and evaporated. The solid residue was triturated in EtOH (5 mL) at RT for 15 min. The suspension was filtered. The filtrate was analyzed by MS showing a number of compounds including the SM, the mono-, di- and tri-adducts. The filtrate was evaporated and further dried under high vacuum to give 0.247 g as a light yellow solid. The solid from filtration was triturated in MeOH (2 mL) in an ice bath for 30 min and filtered. The filtrate was evaporated and further dried under high vacuum to give 0.165 g as a white solid, lot A-383-65B. $^1$HNMR (300 MHz, D20): δ 4.24-4.30 (m, 2H), 4.17-4.23 (m, 2H), 3.87 (s, 6H). ESI-HRMS: 123.0470 (M$^+$).

(2-hydroxyethyl) dimethylsulfoxonium with a halide counterion may be isolated from natural sources, for example from plants of the genus *Mikania*. Alternatively, (2-hydroxyethyl) dimethylsulfoxonium with a halide counterion may be chemically synthesized. The halide may be selected from fluoride, chloride, bromide or iodide.

Example 10: Assays for Identifying and Characterizing Compounds that Inhibit the Formation of TMA from Choline This example provides an exemplary assay for identifying and characterizing compounds that inhibit the formation of TMA from choline.

*Proteus mirabilis* 29906 (Pm) strain was grown aerobically overnight in 500 ml of Nutrient Broth media (3 g/L beef extract, 5 g/L Peptone; Difco #234000) at 37° C. with 250 rpm shaking. The biomass was pelleted by centrifugation at 6000×g for 12 minutes at 4° C. The cell pellet was suspended in 240 mL of ice-cold 1× Phosphate Buffered Saline (Ca$^{2+}$ and Mg$^{2+}$ free). Ninety micrograms of Lysozyme (Sigma #L6876 Lot #SLBG8654V; Sigma-Aldrich Corp., St. Louis, Mo.) was added and incubated with 320 rpm shaking for 30 minutes at 4° C. Lysis was achieved via French press with a 4° C. prechilled 1" diameter chamber at 1000 psi (high ratio; internal PSI equivalent ~16000). The lysate was centrifuged at 6,000×g for 12 minutes at 4° C. to pellet extra debris. A protein concentration of the centrifuged lysate supernatant was determined by a BCA Protein Assay Kit (Pierce #23225; Thermo Fisher Scientific Co., Waltham, Mass.) and protein concentration adjusted to 3 mg/ml with 1× Dulbecco's phosphate buffered saline (DPBS). The centrifuged supernatant lysate was aliquoted into 20 mL volumes and stored frozen at −80° C.

*Proteus mirabilis* 29906 (Pm) lysate was diluted to 1.5 mg/mL protein with 1×DPBS. Choline chloride (CC) (1M stock) was added to reach a final concentration of 2.5 mM choline chloride. The mixture was mixed using a vortex mixer for approximately 15 seconds and incubated at 37° C. for 22 hours. After incubation, 150 µL of CC-treated Pm lysate was dispensed into a deep-well plate (polypropylene, 2 mL volume, Corning Axygen catalogue #P-DW-20-C). Candidate IC$_{50}$ compounds, for example (2-hydroxyethyl) dimethylsulfonium chloride resuspended in water, and vehicle control (respective vehicle control or water), or control compounds (IC$_{50}$ control, 8-Quinolinol hemisulfate salt (Sigma Catalog #55100)) were added at a 1:100 dilution (e.g., 1.5 µL per well). The plates were agitated on a plate shaker for 1 minute. d9-choline chloride (1.5 µL of 5 mM, Cambridge Isotope Laboratories, Inc., USA, choline chloride (trimethyl-D9, 98%), catalog #DLM-549) was added to all wells to reach a final d9-choline chloride concentration of 50 µM.

The plates were again agitated on a plate shaker for 1 minute and incubated at 37° C. for two hours. After incubation, 1.5 µL of formic acid was added to each well (final concentration=1% formic acid). The plates were agitated on a plate shaker for 1 minute and placed on ice. Cell lysate samples were spiked with stable isotope labeled internal standard (22.5 µL of 6 µg/mL of 13C3-trimethylamine (13C3-TMA) was added to each sample), then d9-trimethylamine (d9-TMA), trimethylamine (TMA) and 13C3-TMA were isolated from the lysate after protein precipitation as described below. Acetonitrile acidified with 0.1% formic acid, 600 µL, was added to each sample which was then centrifuged (2,100 g for 20 minutes) to pellet the protein and other precipitates. The supernatant was removed and analyzed as described below. The TMA, d9-TMA and 13C3-TMA in the isolated supernatant samples were subjected to gradient High Performance Liquid Chromatography (HPLC) analysis on a Waters Atlantis HILIC Silica column, from Waters Corp., Milford, Mass., (2.1×50 mm, 3 µm particles) with an Atlantis Silica HILIC Sentry guard column, from Waters Corp., Milford, Mass., (100 Å, 3 µm, 2.1 mm×10 mm), 10 mM ammonium formate in water with 0.1% formic acid as mobile phase A and 0.1% formic acid in acetonitrile as mobile phase B. Detection and quantitation was achieved by tandem mass spectrometry operating under multiple reaction monitoring (MRM) MS/MS conditions (m/z 60.1→44.1 for TMA, m/z 69.1→49.1 for d9-TMA, m/z 63.0→46.1 for 13C3-TMA). TMA and d9-TMA calibration standards (STD), prepared in 80/20/0.1% acetonitrile/Water/Formic Acid, were used to construct a regression curve by plotting the response (peak area TMA/peak area 13C3-TMA) versus concentration for each standard. The concentrations of TMA and d9-TMA in the cell lysate were determined by interpolation from the quadratic (1/x2) regression curve.

In various embodiments, the compound demonstrates an $IC_{50}$ of $1\times10^{-3}$ or less, $5\times10^{-3}$ or less, $1\times10^{-4}$ or less, $5\times10^{-4}$ or less, $1\times10^{-5}$ or less, $5\times10^{-5}$ or less, or $1\times10^{-6}$ or less, or $1\times10^{-7}$ or less, or $1\times10^{-8}$ or less, or $1\times10^{-9}$ or less, or $1\times10^{-10}$ or less or $1\times10^{-11}$ or less or $1\times10^{-12}$ or less, or between $1\times10^{-9}$ and $1\times10^{-3}$, or between $1\times10^{-12}$ and $1\times10^{-9}$, or between $1\times10^{-9}$ and $1\times10^{-6}$, or between $1\times10^{-8}$ and $1\times10^{-6}$, or between $1\times10^{-6}$ and $1\times10^{-3}$, between $1\times10^{-6}$ and $1\times10^{-4}$, between $1\times10^{-6}$ and $1\times10^{-5}$, between $1\times10^{-5}$ and $1\times10^{-3}$, or between $1\times10^{-4}$ and $1\times10^{-3}$, or between $1.7\times10^{-11}$ and $1\times10^{-7}$, (observed 50% inhibition of TMA (or TMAO) formation from choline; mol/L), in the assays described in EXAMPLE 2 or EXAMPLE 5. In various embodiments, the compound demonstrates an $IC_{50}$ of between $1\times10^{-11}$ and $1\times10^{-7}$, or between $1\times10^{-8}$ to $1\times10^{-3}$, or between $1.2\times10^{-6}$ to $2\times10^{-3}$, or between $1\times10^{-6}$ to $1\times10^{4}$ (observed 50% inhibition of TMA formation from choline; mol/L) as measured in the assays described in EXAMPLE 10 or EXAMPLE 11.

$IC_{50}$ measurements for inhibition of conversion of choline to TMA, as outlined in EXAMPLE 10, for compounds are set forth in TABLE 10.

TABLE 10

| Compound Name | SMILES | TMA Inhibition ($IC_{50}$, mol/L) |
|---|---|---|
| (2-hydroxyethyl) dimethylsulfoxonium chloride | C[S+](C)(CCO)=O•[Cl⁻] | 7.74E−09 |

EXAMPLE 10 provides exemplary methods of identifying and quantitating TMA in a sample, as well as screening candidate inhibitory compounds. All compounds in TABLE 10 were found to inhibit the conversion of choline to TMA.

Example 11: Polymicrobial Screening Method

Human fecal polymicrobial incubation with deuterium labeled choline compound screening method, including cell viability assay. All materials were pre-reduced in an anaerobic chamber for 24 hours before using in the experiments and experimental procedures were performed under anaerobic conditions (chamber purged with 85% nitrogen, 5% hydrogen, 10% carbon dioxide).

Human fecal samples were collected from a healthy male volunteer with no chronic illnesses, blood borne diseases or active infections. The volunteer had not received antibiotics within two months prior to donation and provided written informed consent. Samples were diluted to make a 20% (w/v) fecal slurry by resuspension of the feces in a media containing 3% (w/v) tryptic soy broth (BBL #211825), 1% (w/v) trehalose (Sigma #T9631), pH 7.3. The fecal slurry was homogenized and filtered by hand using a stomacher bag with an integrated 170 μm membrane. DMSO (5% (w/v)) was added to the filtered slurry and aliquots were stored in cryogenic vials at −80° C. until use. Frozen fecal slurries were diluted to 0.2% (w/v) with M9 media ($Na_2HPO_4$ (6 g/L), $KH_2PO_4$ (3 g/L), NaCl (0.5 g/L) with addition of 0.1 mM $CaCl_2$) and 1 mM $MgSO_4$) and dispensed (1 mL) into deep well 96-well plates. Diluted fecal slurries containing 50 μM d9-choline chloride and compounds in doses ranging from 250 μM to 0.238 nM were sealed and incubated at 37° C. with shaking. Vehicle control was water and positive control compound was 8-Quinolinol hemisulfate salt. After 20 hours, an aliquot of the fecal polymicrobial community was analyzed for viability using PrestoBlue cell viability reagent (Thermo Fisher Scientific, USA) as described below. The reaction plates were subsequently centrifuged (4000×g at 4° C. for 12 min) to pellet fecal material and 150 μl aliquots were transferred and quenched with addition of formic acid to 1% (v/v). All fecal processing and polymicrobial assay steps were performed in an anaerobic environment. The products were determined by LC/MS/MS and $IC_{50}$ values were calculated as described previously for detection and analysis of TMA and d9-TMA in EXAMPLE 9.

$IC_{50}$ measurements for inhibition of conversion of choline to TMA, as outlined in EXAMPLE 11, for compound (2-hydroxyethyl) dimethylsulfonium chloride are set forth in TABLE 11.

TABLE 11

| Compound Name | SMILES | TMA Inhibition ($IC_{50}$, mol/L) |
|---|---|---|
| (2-hydroxyethyl) dimethylsulfoxonium chloride | C[S+](C)(CCO)=O•[Cl⁻] | 9.734E−08 |

For the PrestoBlue cell viability assay, a 6 μL aliquot of the fecal polymicrobial community assay was added to 84 μL M9 media in a black, clear bottom 96 well plate. To this was added 10 μL of PrestoBlue reagent, covered and shaken for 1 minute at 800 rpm. The plates were incubated at 37° C. for 30 minutes and fluorescence read following the manufacturer's instructions. Cell viability was calculated as % fluorescence compared to vehicle control (e.g. water).

TABLE 12 cell viability data as determined in EXAMPLE 11, compound (2-hydroxyethyl) dimethylsulfonium chloride, in the PrestoBlue assay. Maximum concentration tested is reported, along with lowest concentration tested at which cell viability was determined to be 10% or lower, compared to vehicle control. If cell viability was not determined to be 10% or lower at any of the concentrations tested, the cell is marked N/A.

TABLE 12

| Name (INCLUDING COUNTERION) | SMILES (INCLUDING COUNTERION) | Maximum Concentration Tested (μM) | Lowest concentration tested at which cell viability was 10% or lower (μM) |
|---|---|---|---|
| (2-hydroxyethyl) dimethylsulfoxonium chloride | C[S+](C)(CCO)=O•[Cl⁻] | 250 | N/A |

EXAMPLE 11 provides exemplary methods of screening candidate inhibitory compounds for the conversion of choline to TMA and for calculation of cell viability.

In various embodiments, the inhibition of conversion of choline to TMA by the (2-hydroxyethyl) dimethylsulfonium chloride is not brought about by an antibiotic mechanism of action, for example it is not brought about by an antibacterial mechanism of action, or by a mechanism of action which reduces cell viability to 10% or lower, when compared to vehicle control.

Example 12: Rapid Preclinical Method to Determine Compound Efficacy

Challenge: C57bl/6 female mice (8 wk of age ~20 g BW) were maintained in accordance with the NIH guidelines in a 12:12 hr light:dark cycle on normal chow diet were placed in a clean cage without food ~1 hr prior to gavage. Mice were given 2 mg d9-Choline+x mg/kg inhibitor (where x=0 to 100 mg/kg) in water by oral gavage using a 1.5" 22 G ball-tip curved feeding needle to administer compound in 200 μl of water. Food was returned after a 2 hr fast (1 hr after gavage administration). Blood (30 μL) was collected into a heparinized capillary tube 2, 3 and 4 hours after gavage. Blood was kept at 4° C., then spun using a centrifuge (5 min in centrifuge designed to capillary tubes) to separate plasma and hematocrit within 4 hours after collection. Plasma samples were stored at −80° C. Concentration of d9 Choline, d9TMA and d9TMAO was measured by LC-MS/MS.

Flora Normalization: Twenty four hours post-gavage mice were placed in a clean cage and fecal material from conventional mice was spread in all the cages.

EXAMPLE 12 provides exemplary methods of screening candidate inhibitory compounds for the conversion of choline to TMA.

$EC_{50}$ measurements (Concentration to provide 50% effective inhibition) for inhibition of plasma levels of TMAO, compared to vehicle control, as outlined in EXAMPLE 12 for (2-hydroxyethyl) dimethylsulfonium chloride is set forth in TABLE 13.

TABLE 13

Calculated $EC_{50}$ (mg/kg) for inhibition of TMAO production, compared to Vehicle Control, as described in EXAMPLE 12.

| Compound Name | $EC_{50}$ (mg/Kg) | Time |
| --- | --- | --- |
| (2-hydroxyethyl) dimethylsulfonium chloride | 0.06 | 3 h |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

```
                        SEQUENCE LISTING

<160> NUMBER OF SEQ ID NOS: 2

<210> SEQ ID NO 1

<211> LENGTH: 419

<212> TYPE: DNA

<213> ORGANISM: Mikania guaco
ETS (external transcribed spacer) region

<400> SEQUENCE: 1
actttcctct ttgacgtaac ccaacgccct ggcacaagcc aatgcgagtt gagcagtcgt
atacgagaag cataaccagg acataaaagg aactcacgaa acccatgccc acatcagttc
cataccaaag ataccaagca Attaccaatg taccacatca ccagacaagc atcagagagg
tggttcaagg agttgccttc atggttcatc cgatctcata aagtacaaga caagacgaaa
gaacttatac cagccaacaa aagtaccaca tgataggtag gcaacacagg aaacccacaa
tctgttttag caatagaagc cttaacagac aaatgaaaag gtatgtcagg tggaagttgt
tgcacaagca aagagccaac caccagtaac aaaccaaaca ccactcatgc acctttacg

<210> SEQ ID NO 2

<212> LENGTH: 714

<213> TYPE: DNA
```

SEQUENCE LISTING

<214> ORGANISM: *Mikania guaco*
ITS (internal transcribed spacer) region

<400> SEQUENCE: 2
aagtcgtaac aaggtttccg taggtgaacc tgcggaagga tcattgtcga atcctgcgta
gcagaacaac ctgtgaacgt gtaacaacaa aatggcttca ctgggggtgt tgcttttgtt
tcagaccctg tgaagccttt tcagcacgtg tttgtggttg cctgtttcgg tcactcatgg
atgtcgtgct gatgtaacaa ccccccggca caacatgtgc caaggaaatc aaatcttaag
agggcatgtg ccatgacacc ccgtacgtgg tgtgtttgtc gtatgtggcc cctatgtaaa
atcttaaaac aactctcggc aacggatatc ttggctcacg catcgatgaa gaacgtagca
aaatgcgata cttggtgtga attgcagaat cccgtgaacc atcgagtttt tgaacgcaag
ttgcgcccga agccacttgg ttgagggcac gtctgcctgg gtgtcacgca tcatgtcgcc
caaatcaaac ttaccttagg gtactgtgtt gtatgtaggg cggagactgg tctcctatgc
ccatggcgtg gttggccgaa atacgagtcc cttgacgagt gacgcatgac tggtggtggt
tgattagaca gtcgtcctgt gtcgtgcgtt tataattgtg atgggaaaag gctcttaaaa
taccctgata tgtgttgtct agtgacaatt gtttgattgc gaccccaggt cagg

---

SEQUENCE LISTING

<160> NUMBER OF SEQ ID NOS: 2

<210> SEQ ID NO 1
<211> LENGTH: 419
<212> TYPE: DNA
<213> ORGANISM: Mikania guaco

<400> SEQUENCE: 1

| | | | | | |
|---|---|---|---|---|---|
| actttcctct | ttgacgtaac | ccaacgccct | ggcacaagcc | aatgcgagtt | gagcagtcgt | 60 |
| atacgagaag | cataaccagg | acataaaagg | aactcacgaa | acccatgccc | acatcagttc | 120 |
| cataccaaag | ataccaagca | attaccaatg | taccacatca | ccagacaagc | atcagagagg | 180 |
| tggttcaagg | agttgccttc | atggttcatc | cgatctcata | aagtacaaga | caagacgaaa | 240 |
| gaacttatac | cagccaacaa | aagtaccaca | tgataggtag | gcaacacagg | aaacccacaa | 300 |
| tctgttttag | caatagaagc | cttaacagac | aaatgaaaag | gtatgtcagg | tggaagttgt | 360 |
| tgcacaagca | aagagccaac | caccagtaac | aaaccaaaca | ccactcatgc | acctttacg | 419 |

<210> SEQ ID NO 2
<211> LENGTH: 714
<212> TYPE: DNA
<213> ORGANISM: Mikania guaco

<400> SEQUENCE: 2

| | | | | | |
|---|---|---|---|---|---|
| aagtcgtaac | aaggtttccg | taggtgaacc | tgcggaagga | tcattgtcga | atcctgcgta | 60 |
| gcagaacaac | ctgtgaacgt | gtaacaacaa | aatggcttca | ctgggggtgt | tgcttttgtt | 120 |
| tcagaccctg | tgaagccttt | tcagcacgtg | tttgtggttg | cctgtttcgg | tcactcatgg | 180 |
| atgtcgtgct | gatgtaacaa | ccccccggca | caacatgtgc | caaggaaatc | aaatcttaag | 240 |
| agggcatgtg | ccatgacacc | ccgtacgtgg | tgtgtttgtc | gtatgtggcc | cctatgtaaa | 300 |
| atcttaaaac | aactctcggc | aacggatatc | ttggctcacg | catcgatgaa | gaacgtagca | 360 |
| aaatgcgata | cttggtgtga | attgcagaat | cccgtgaacc | atcgagtttt | tgaacgcaag | 420 |
| ttgcgcccga | agccacttgg | ttgagggcac | gtctgcctgg | gtgtcacgca | tcatgtcgcc | 480 |

-continued

```
caaatcaaac ttaccttagg gtactgtgtt gtatgtaggg cggagactgg tctcctatgc      540
ccatggcgtg gttggccgaa atacgagtcc cttgacgagt gacgcatgac tggtggtggt      600
tgattagaca gtcgtcctgt gtcgtgcgtt tataattgtg atgggaaaag gctcttaaaa      660
taccctgata tgtgttgtct agtgacaatt gtttgattgc gaccccaggt cagg            714
```

What is claimed is:

1. A method of improving a disease or a condition associated with the conversion of choline to trimethylamine (TMA) in an individual comprising administering to the individual (2-hydroxyethyl) dimethylsulfoxonium;
    wherein the (2-hydroxyethyl) dimethylsulfoxonium is administered in an amount effective to treat or prevent the disease or condition associated with choline-related trimethylamine (TMA) in the individual.

2. The method of claim 1, wherein the disease or condition associated with the conversion of choline to trimethylamine is a cardiovascular disease, trimethylaminuria, reduced or impaired kidney function, kidney disease, chronic kidney disease, end-stage renal disease, obesity, insulin resistance, diabetes mellitus, Alzheimer's disease, dementia, cognitive impairment, or non-alcoholic steatohepatitis (NASH).

3. The method of claim 2, wherein the cardiovascular disease is selected from the group consisting of angina, arrhythmia, atherosclerosis, cardiomyopathy, congestive heart failure, coronary artery disease (CAD), carotid artery disease, endocarditis, coronary thrombosis, myocardial infarction (MI), high blood pressure/hypertension, hypercholesterolemia/hyperlipidemia, mitral valve prolapsed, peripheral artery disease (PAD), and stroke.

4. A method of inhibiting the conversion of choline to trimethylamine (TMA) and reducing TMAO level in an individual comprising administering to the individual a composition comprising (2-hydroxyethyl) dimethylsulfoxonium;
    wherein the composition is administered in an amount effective to inhibit formation of trimethylamine (TMA) from choline in the individual.

5. The method of claim 4, comprising administering the composition to an individual having an elevated level of TMAO in blood, plasma, serum, or urine, or combinations thereof.

* * * * *